US012186524B2

(12) United States Patent
Nemoto et al.

(10) Patent No.: US 12,186,524 B2
(45) Date of Patent: Jan. 7, 2025

(54) CHEMICAL LIQUID INJECTOR

(71) Applicant: Nemoto Kyorindo Co., Ltd., Tokyo (JP)

(72) Inventors: Shigeru Nemoto, Tokyo (JP); Tsuyoshi Saito, Tokyo (JP)

(73) Assignee: Nemoto Kyorindo Co., Ltd., Tokyo (JP)

( * ) Notice: Subject to any disclaimer, the term of this patent is extended or adjusted under 35 U.S.C. 154(b) by 1150 days.

(21) Appl. No.: 16/603,543

(22) PCT Filed: Apr. 11, 2018

(86) PCT No.: PCT/JP2018/015205
§ 371 (c)(1),
(2) Date: Oct. 7, 2019

(87) PCT Pub. No.: WO2018/190367
PCT Pub. Date: Oct. 18, 2018

(65) Prior Publication Data
US 2020/0030524 A1 Jan. 30, 2020

(30) Foreign Application Priority Data
Apr. 12, 2017 (JP) ................................ 2017-079145

(51) Int. Cl.
*A61M 5/00* (2006.01)
*A61B 5/055* (2006.01)
(Continued)

(52) U.S. Cl.
CPC ............. *A61M 5/007* (2013.01); *A61B 5/055* (2013.01); *A61B 6/481* (2013.01); *A61M 5/1408* (2013.01);
(Continued)

(58) Field of Classification Search
CPC .............. B01F 2101/2202; B01F 25/10; B01F 33/50112; B01F 33/5014; B01F 35/2209;
(Continued)

(56) References Cited

U.S. PATENT DOCUMENTS

2012/0053457 A1* 3/2012 Fago ................. A61M 5/14546
600/432

FOREIGN PATENT DOCUMENTS

EP   3 111 975 A1   1/2017
JP   2014-500775 A   11/2010
(Continued)

OTHER PUBLICATIONS

International Preliminary Report on Patentability issued in International Application No. PCT/JP2018/015205, mailed Oct. 15, 2019.
(Continued)

*Primary Examiner* — Brandy S Lee
(74) *Attorney, Agent, or Firm* — Knobbe, Martens, Olson & Bear, LLP

(57) ABSTRACT

A chemical liquid injector that can easily set various injection conditions according to a region and an objective to be imaged. The chemical liquid injector includes two piston driving mechanisms for operating syringes filled with a first chemical liquid and a second chemical liquid, respectively, an input unit for receiving an input of a data, and an injection control unit for controlling an operation of the piston driving mechanisms. The injection control unit is set with a multi-stage injection mode in which injection operations are performed in a plurality of injection phases. In the multi-stage injection mode, the injection control unit is configured to receive the input of the mixing rate of the first chemical liquid and the second chemical liquid for each of the plurality of injection phases, set injection conditions of the first chemical liquid and the second chemical liquid so that (Continued)

the first chemical liquid and the second chemical liquid are injected at the received mixing rate, and control the operation of the driving mechanisms according to the set injection condition.

16 Claims, 11 Drawing Sheets

(51) Int. Cl.
| | |
|---|---|
| *A61B 6/00* | (2006.01) |
| *A61M 5/14* | (2006.01) |
| *A61M 5/145* | (2006.01) |
| *A61M 5/168* | (2006.01) |
| *A61M 5/172* | (2006.01) |
| *B01F 25/10* | (2022.01) |
| *B01F 33/501* | (2022.01) |
| *B01F 35/22* | (2022.01) |
| *B01F 101/00* | (2022.01) |

(52) U.S. Cl.
CPC ...... *A61M 5/1409* (2013.01); *A61M 5/14546* (2013.01); *A61M 5/16813* (2013.01); *A61M 5/172* (2013.01); *B01F 25/10* (2022.01); *B01F 33/50112* (2022.01); *B01F 35/2209* (2022.01); *A61M 2005/14506* (2013.01); *A61M 2205/3379* (2013.01); *A61M 2205/50* (2013.01); *A61M 2205/505* (2013.01); *A61M 2205/6054* (2013.01); *A61M 2205/80* (2013.01); *B01F 2101/2202* (2022.01)

(58) Field of Classification Search
CPC ........... A61M 2005/14506; A61M 2039/2406; A61M 2205/3379; A61M 2205/3569; A61M 2205/50; A61M 2205/505; A61M 2205/6054; A61M 2205/80; A61M 2206/16; A61M 5/007; A61M 5/1408; A61M 5/1409; A61M 5/14546; A61M 5/16813; A61M 5/16827; A61M 5/172; A61B 5/055; A61B 6/481
See application file for complete search history.

(56) References Cited

FOREIGN PATENT DOCUMENTS

| | | | |
|---|---|---|---|
| WO | WO 2006/068171 | 6/2006 | |
| WO | WO 2007/116840 | 10/2007 | |
| WO | WO 2007/116865 | 10/2007 | |
| WO | WO 2012/071307 | 5/2012 | |
| WO | WO 2014/168206 | 10/2014 | |
| WO | WO-2014168206 A1 * | 10/2014 | ........ A61M 5/14546 |
| WO | WO 2015/129227 A1 | 9/2015 | |
| WO | WO 2016/208611 | 12/2016 | |

OTHER PUBLICATIONS

Office Action in Japanese Patent Application No. 2022-018433, mailed Jan. 17, 2023.
Office Action in related Japanese Application No. 2019-512548 mailed on Oct. 12, 2021.
Office Action in Japanese Patent Application No. 2023-085002 issued on Oct. 25, 2024 & English translation in 9 pages.

* cited by examiner

CHEMICAL LIQUID INJECTOR

This application is the U.S. National Phase under 35 U.S.C. § 371 of International Application PCT/JP2018/015205, filed Apr. 11, 2018, designating the U.S., and published in Japanese as WO 2018/190367 on Oct. 18, 2018 which claims priority to Japanese Patent Application No. 2017-079145, filed Apr. 12, 2017, the entire content of which is incorporated herein by reference.

TECHNICAL FIELD

The present invention relates to a chemical liquid injector for injecting a chemical liquid filled in a container such as a syringe.

BACKGROUND ART

Currently, CT (Computed Tomography) scanners, MRI (Magnetic Resonance Imaging) apparatuses, PET (Positron Emission Tomography) apparatuses, ultrasound diagnostic apparatuses, angiography apparatuses (angiography) and the like are known as medical diagnostic imaging apparatuses. In using above mentioned imaging apparatuses, a chemical liquid such as a contrast medium or physiological saline may be injected into a patient using the chemical liquid injector.

In particular, angiography technology using a chemical liquid injector in recent years has developed from a conventional image diagnosis to a treatment technique (IVR: Interventional Radiology) using a diagnostic imaging apparatus with the development of X-ray equipment, catheters, contrast agents and the like. Considering each procedure, the procedure can be divided into local injection (arterial injection) of a chemical liquid using a catheter, embolization of a blood vessel, dilation and opening of a blood vessel. Subjects include tumors, bleeding, vascular lesions and the like. For tumors, there are intra-arterial injection of anticancer drugs and transcatheter arterial embolization (TAE). For bleeding, there are continuous arterial infusion of vasoconstrictors and arterial embolization, and for vascular lesions, there are thrombolysis and percutaneous transluminal angioplasty (PTA).

Percutaneous transluminal coronary angioplasty (PTCA) is rapidly developing among the percutaneous transluminal angioplasties currently performed actively. PTCA can be broadly divided into balloon catheters, atherectomy (coronary atherectomy) and stent implantation. From the background of the evolution of angiography, there is a demand for reliable treatment as well as diagnostic imaging by selectively imaging various blood vessels directly connected to organs and lesions in the head, chest (including heart), abdomen, and lower limbs, or imaging the same blood vessel many times (in order to confirm complicated blood vessel paths, change the imaging angle to know the antero-posterior relationship of the blood vessels, finely adjust the injection conditions so that the catheter cannot be removed, and check after treatment).

Under such a background, an angiographic apparatus capable of acquiring a tomographic image similar to that of a CT apparatus has been put into practical use. As a result, even though a CT tomographic image is required during an examination by the angiographic apparatus, a desired image can be obtained only by the angiographic apparatus. Therefore, examinations and treatments combining such angiography and tomographic imaging are expected to increase further in the future.

As described above, the examination using the angiography apparatus is different from CT examination and MR examination in that the contrast medium is repeatedly injected while appropriately adjusting the concentration and flow rate of the contrast medium according to the blood vessel region.

For example, Patent Literature 1 discloses an example of a chemical liquid injector for angiography. This chemical liquid injector is used for a catheter angiography, for example. In a catheter method, a catheter is percutaneously introduced into a blood vessel (artery) by a guide wire without incising the skin. Then, after the distal end of the catheter is positioned in the vicinity of the start portion of the target blood vessel, the chemical liquid injector is operated to inject a contrast medium using a predetermined injection protocol, and continuous imaging is performed using the imaging apparatus. As a result, an image representing the contrasted blood vessel is displayed on a predetermined display, and the doctor diagnoses and treats while viewing the image.

As a chemical liquid injector for angiography, for example, as disclosed in Patent Literature 1, an apparatus including an injection head and a console is known. The injection head for angiography has the following characteristics that are different from the injection head for CT examination and MR examination. That is, the angiography has a feature that the injection pressure becomes very high because the chemical liquid is injected through an elongated catheter introduced into the blood vessel. Therefore, many syringes are configured to be attached to the injection head in a state where the syringe is put in a protective cover or the like. This is different from an injection head for CT examination or MR examination in which a syringe is directly mounted or mounted via an adapter that holds a part of the syringe.

Patent Literature 2 discloses a chemical liquid injection device for angiography in which two syringes can be attached and a contrast medium and physiological saline can be injected simultaneously. According to the chemical liquid injector described in Patent Literature 2, the contrast medium can be diluted with physiological saline and injected. Therefore, it is possible to easily change the concentration of the contrast medium according to the blood vessel region without replacing the syringe.

CITATION LIST

Patent Literature

Patent Literature 1: PCT International Publication No. WO 2006/068171
Patent Literature 2: PCT International Publication No. WO 2016/208611

SUMMARY OF INVENTION

Technical Problem

However, in a conventional chemical liquid injector for angiography, even though the contrast medium can be diluted with physiological saline as described in Patent Literature 2, the concentration of the contrast medium injected in one injection operation cannot be changed, and the setting of injection conditions was limited. Therefore, for example, in hepatic arteriography, since the thickness of the blood vessel is too different between the proximal side and the distal side of the blood vessel, there may be a problem that the proximal side is produced well but the distal side is not produced or the distal side is produced well but the proximal side has too large artifact. In addition, for example, when it is desired to know a malformed region by examining a cerebral artery malformation, it is advantageous that imaging can be performed with contrast so that the artery and the vein can be distinguished. However, it is difficult to image with contrast in the case of injecting the contrast medium at a constant concentration.

It is an object of the present invention to provide a chemical liquid injector which can set easily various injection conditions according to a region and an objective to be imaged.

Solution to Problem

According to an aspect of the present invention, provided is a chemical liquid injector for injecting a chemical liquid filled in a container comprising:
a first driving mechanism configured to make a first chemical liquid flow out of a first container filled with the first chemical liquid,
a second driving mechanism configured to make a second chemical liquid flow out of a second container filled with the second chemical liquid, at least one data input interface which receives an input of data, and
an injection controller configured to control an operation of at least the first driving mechanism and the second driving mechanism,
wherein at least a multistage injection mode for performing a series of injection operation in a plurality of injection phase is set in the injection controller as one of at least one injection mode of the chemical liquid, and
the injection controller is configured to:
receive the input of a mixing rate of the first chemical liquid and the second chemical liquid through the data input interface for each of the plurality of injection phase in the multistage injection mode,
set injection conditions of the first chemical liquid and the second chemical liquid so that the first chemical liquid and the second chemical liquid are injected at the received mixing rate, and
control the operation of the first driving mechanism and the second driving mechanism according to the set injection conditions.

According to another aspect of the present invention, provided is a chemical liquid injection system comprising:
anyone of the above described chemical liquid injector,
a first container and a second container detachably mounted on the chemical liquid injector, and
an injection circuit connected to the first container and the second container.

According to still another aspect of the present invention, provided is a diagnostic imaging system comprising:
anyone of the above described chemical liquid injection system,
a diagnostic imaging apparatus for obtaining a medical image from a patient into which a chemical liquid has been injected by the chemical liquid injection system.

According to still another aspect of the present invention, provided is an operation method of a chemical liquid injector for injecting a chemical liquid filled in a container comprising a first driving mechanism configured to make a first chemical liquid flow out of a first container filled with the first chemical liquid, a second driving mechanism configured to make a second chemical liquid flow out of a second container filled with the second chemical liquid, at least one data input interface which receives an input of data, and an injection controller configured to control an operation of at least the first driving mechanism and the second driving mechanism, wherein at least a multistage injection mode for performing a series of injection operation in a plurality of injection phase is set in the injection controller as one of at least one injection mode of the chemical liquid, the operation method comprising:
receiving the input of a mixing rate of the first chemical liquid and the second chemical liquid through the data input interface for each of the plurality of injection phase in the multistage injection mode by the injection controller,
setting injection conditions of the first chemical liquid and the second chemical liquid by the injection controller so that the first chemical liquid and the second chemical liquid are injected at the received mixing rate, and
controlling the operation of the first driving mechanism and the second driving mechanism by the injection controller according to the set injection conditions.

Definition of Terms Used in the Present Invention

"Injection circuit" means a path for following a chemical liquid connected to a container such as a syringe for injecting the chemical liquid into a blood vessel of a patient, and includes a catheter that is inserted into the blood vessel of the patient or an intravenous cannula that is pierced into the blood vessel of the patient. In addition, when a plurality of chemical liquids can be injected, the injection circuit further includes an extension tube branched into a plurality of ends connected to the container, and a distal end of the extension tube is connected to the catheter or the intravenous cannula. Furthermore, at least one member such as another tube may be connected between the extension tube and the catheter or intravenous cannula. The injection circuit can be segmented into an "extracorporeal circuit portion" in which all parts are located outside the body and an "intracorporeal circuit portion" in which at least a part is located in the body, depending on the arrangement in use. According to this segmentation, the catheter or the intravenous cannula belongs to the intracorporeal circuit portion, and the member that connects the container and the portion located outside the body of the intracorporeal circuit portion such as the extension tube belongs to the extracorporeal circuit portion.

"Purge operation" means an operation of discharging the chemical liquid from the container in order to fill the extracorporeal circuit portion of the injection circuit with a desired chemical liquid prior to the injection of the chemical liquid to the patient. When the purge operation also serves the purpose of discharging the air in the container and/or the extracorporeal circuit portion, the purge operation may be referred to as "air releasing". In the purge operation, no chemical liquid is injected into the patient.

Advantageous Effects of Invention

According to the present invention, various injections in which the mixing ratio of the chemicals is changed for each injection phase in accordance with the region to be imaged, the purpose, and the like can be set in a single injection mode by allowing the mixing ratio of the first chemical liquid and the second chemical liquid to be input for each of the first phase and the second phase.

DESCRIPTION OF EMBODIMENTS

Figure 1:
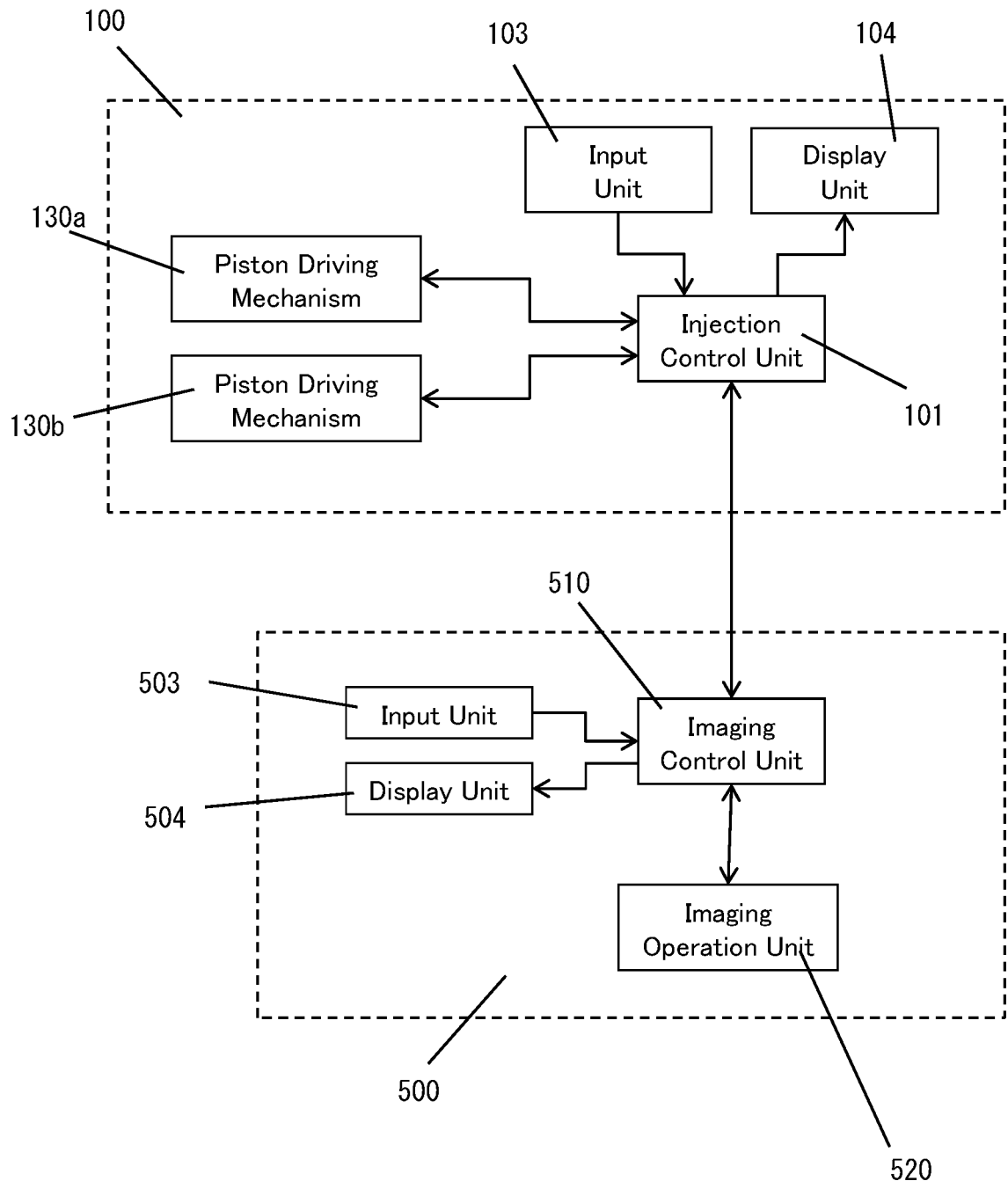
FIG. 1 is a schematic block diagram of a diagnostic imaging system according to an embodiment of the present invention.

Referring to FIG. 1, a block diagram of a diagnostic imaging system according to an embodiment of the present invention is shown, which comprises a chemical liquid injector 100 and a diagnostic imaging apparatus 500. The chemical injection device 100 and the diagnostic imaging apparatus 500 can be connected to each other so that data can be transmitted and received between them. The connection between the chemical liquid injector and the diagnostic imaging apparatus may be a wired connection or a wireless connection. In the following description, it will be described a case where the diagnostic imaging device 500 is an angiography apparatus and the chemical liquid injector 100 is an injector for an angiographic examination suitable for injecting at least a contrast medium as a chemical liquid in the angiographic examination. However, in the present invention, the diagnostic imaging apparatus may be an arbitrary diagnostic imaging apparatus such as an X-ray CT scanner, an MRI apparatus and a PET apparatus, and the chemical liquid injector is also an arbitrary injector that is compatible with these diagnostic imaging apparatuses, as long as a system capable of performing an examination using a plurality of types of chemical liquids can be configured. Therefore, the configuration described in detail below can be appropriately modified according to the types of the diagnostic imaging apparatus and the chemical liquid injector.

The diagnostic imaging device 500 includes an imaging operation unit 520 that performs an imaging operation, and an imaging control unit 510 that controls the operation of the imaging operation unit 520. The diagnostic imaging apparatus 500 can obtain a medical image including a tomographic image and/or a 3D image of a patient into which a chemical liquid is injected by the chemical liquid injector 100. The imaging operation unit 520 includes a bed for the patient, an electromagnetic wave irradiating unit which irradiates electromagnetic waves to a predetermined space on the bed. The imaging control unit 510 controls the operation of the diagnostic imaging apparatus as a whole, such as determining the imaging conditions and controlling the operation of the imaging operation unit 520 according to the determined imaging conditions. The imaging control unit 510 can be configured by a so-called microcomputer, and can have a CPU, a ROM, a RAM, and an interface with other devices. A computer program for controlling the diagnostic imaging apparatus 500 is installed in the ROM. The CPU controls the operation of each part of the diagnostic imaging apparatus 500 by executing various functions corresponding to this computer program.

The fluoroscopic imaging apparatus 500 may further include a display unit 504 such as a liquid crystal display capable of displaying imaging conditions and obtained medical images, and an input unit 503 such as a keyboard and/or mouse for inputting imaging conditions and the like. Data input from the input unit 503 is transmitted to the imaging control unit 510, and data displayed on the display unit 504 is transmitted from the imaging control unit 510. A touch panel in which a touch screen is arranged as an input unit on the display of the display unit can also be used as the input unit 503 and the display unit 504.

The chemical liquid injector 100 is a device used to inject a chemical liquid filled in a syringe as a container into a blood vessel of a patient via an injection circuit, and includes a plurality of piston driving mechanisms 130a and 130b, an input unit. 103, a display unit 104 and an injection control unit 101. The piston driving mechanisms 130a and 130b are mechanisms that operate a piston of the syringe so that the chemical liquid is discharged from the syringe. In this embodiment, two piston drive mechanisms 130a and 130b for independently operating the pistons of the two syringes are provided so that two kinds of chemical liquids can be injected separately or simultaneously. However, there may be a plurality of at least one of the piston driving mechanism 130a for injecting one chemical liquid and the piston driving mechanism 130b for injecting the other chemical liquid.

The injection control unit 101 determines injection conditions such as an injection volume and a flow rate of the chemical liquid, controls the operation of the piston driving mechanisms 130a, 130b so that the chemical liquid is injected from the syringe according to the determined injection conditions and controls the display of the display unit 104, and controls the operation of the chemical solution injector as a whole. The injection control unit 101 can be configured by a so-called microcomputer, and can have a CPU, a ROM, a RAM, and an interface with other devices. A computer program for controlling the chemical liquid injector 100 is installed in the ROM. The CPU controls the operation of each part of the chemical liquid injector 100 by executing various functions corresponding to this computer program.

The input unit 103 is a unit that receives input of data necessary for the injection control unit 101 to determine the injection condition of the chemical liquid and other data. The input unit 103 may be a known input device such as a keyboard and/or a mouse. Data input from the input unit 103 is transmitted to the injection control unit 101 and received by the injection control unit 101. The display unit 104 receives data from the injection control unit 101 and is controlled by the injection control unit 101 to display data necessary for determining the injection condition of the chemical solution, an injection protocol, an injection operation, a warning and the like. The display unit 104 may be a known display device such as a liquid crystal display device. In addition, a touch panel that functions as a data input interface and a display unit in which a touch screen is arranged as an input unit on the display of the display unit can be used as the input unit 103 and the display unit 104.

Next, an example of the appearance and the arrangement of each element of the above-described chemical liquid injector 100 will be described with reference to FIG. 2.

Figure 2:
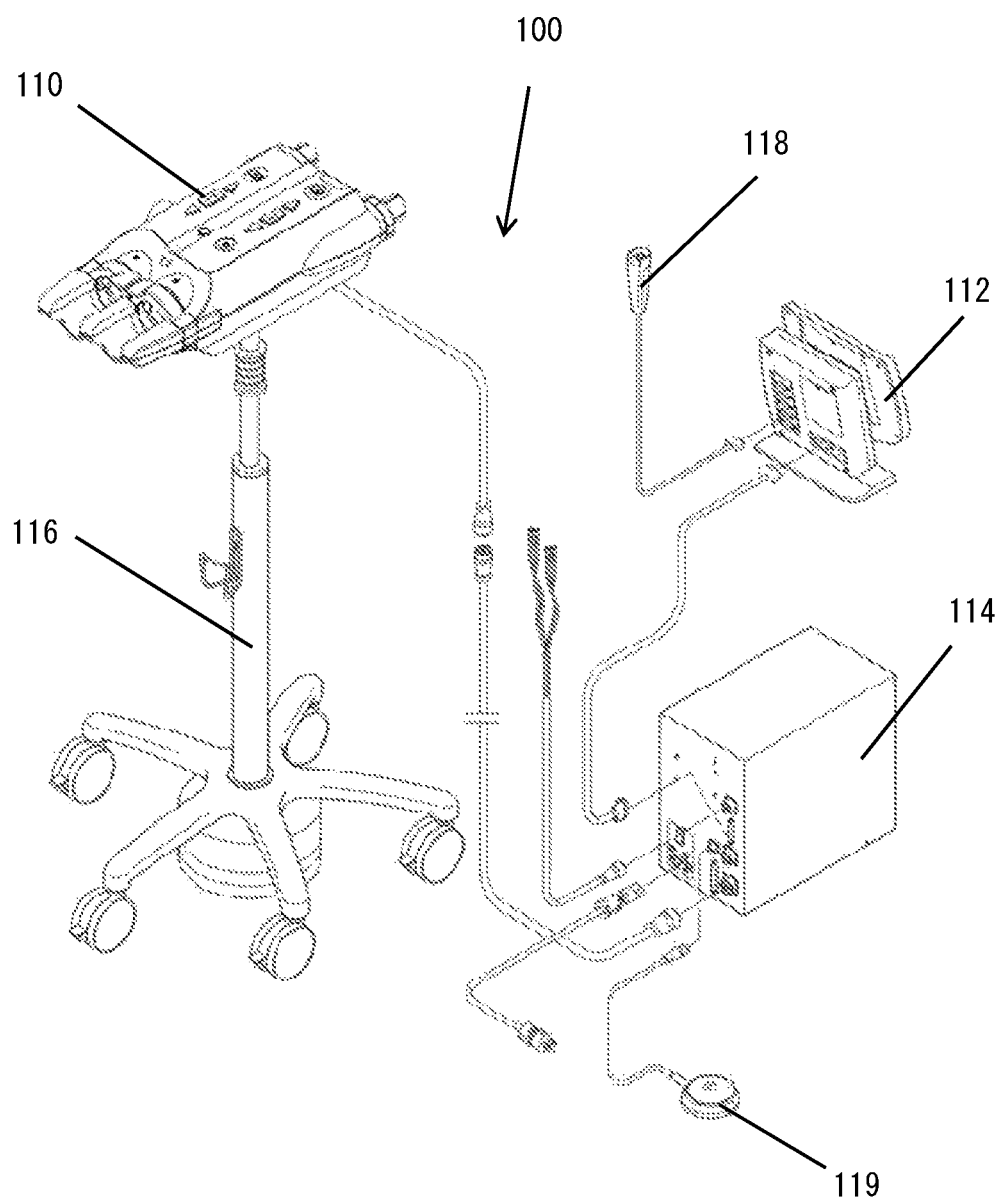
FIG. 2 is a perspective view showing an example of an appearance of a chemical liquid injector according to an embodiment of the present invention.

A chemical liquid injector 100 shown in FIG. 2 is an injector for an angiography apparatus as an example, and comprises an injection head 110, a console 112 and a main unit 114. The injection head 110 and the console 112 are electrically connected via the main unit 114. In the illustrated embodiment, the injection head 110 is supported by the upper part of the stand 116 rotatably, but may be supported by a rotatable arm fixed to the ceiling. The console 112 can include the input unit 103 and the display unit 104 described above. In the illustrated embodiment, the console 112 includes a touch panel, which corresponds to the input unit 103 and the display unit 104 described above. The main unit 114 can include a power supply (not shown) and can supply power to the injection head 110 and the console 112 from this power supply. The injection control unit 101 shown in FIG. 1 may be arranged in the main unit 114 or may be arranged in the console 112.

Figure 3:
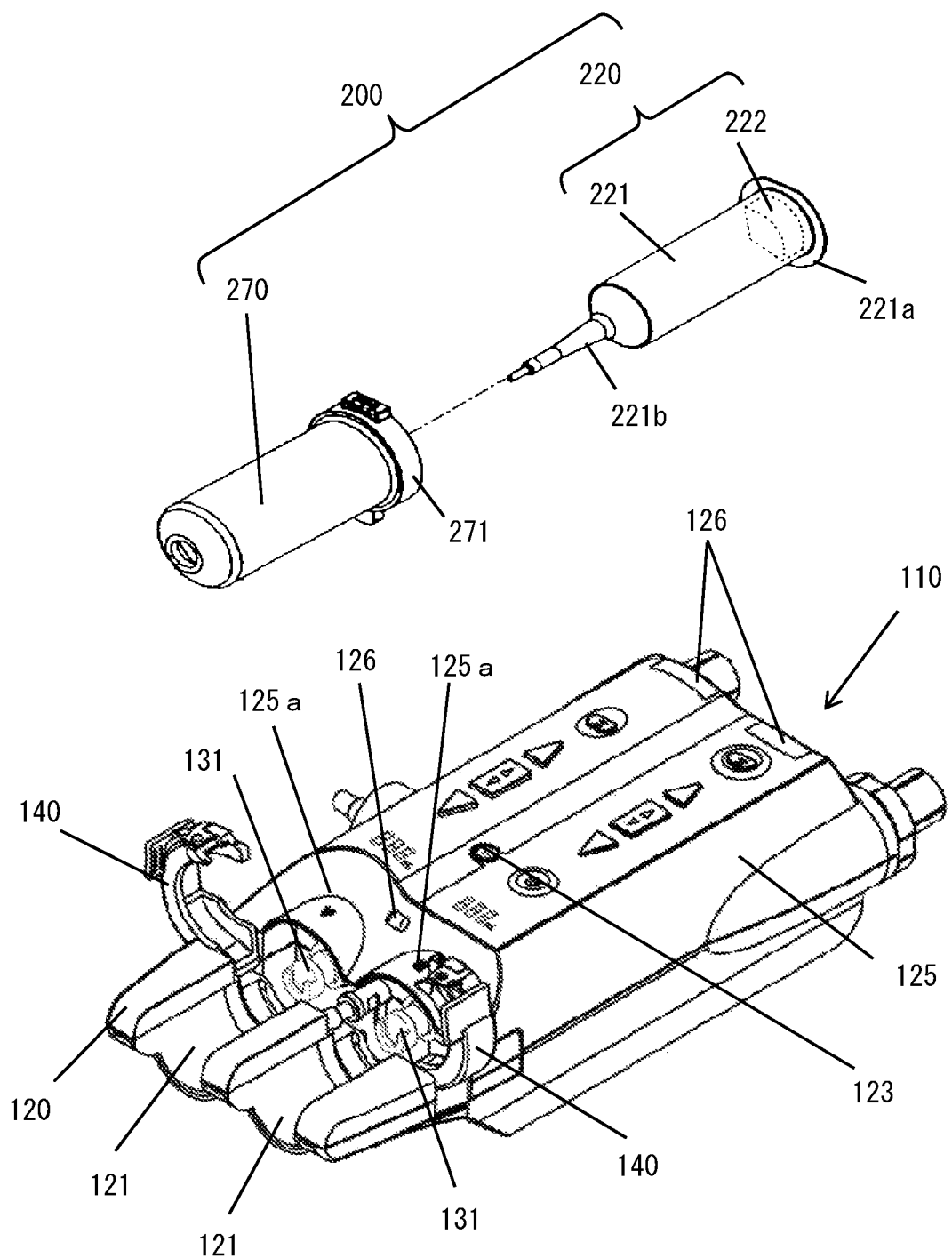
FIG. 3 is a perspective view showing the injection head shown in FIG. 2 together with a syringe assembly mounted on the injection head.

As shown in FIG. 3, the injection head 110 is configured so that two sets of syringe assemblies 200 can be detachably mounted (in FIG. 3, only one set of syringe assemblies 200 is shown for simplicity).

The syringe assembly 200 includes a syringe 220 and a protective cover 270 into which the syringe 220 is inserted. The syringe 220 is generally called a rodless syringe, and has a cylinder 221 having a flange 221a formed at the rear end and a nozzle portion 221b formed at the front end, and a piston inserted into the cylinder 221 so as to be capable of moving forward and backward.

Figure 4:
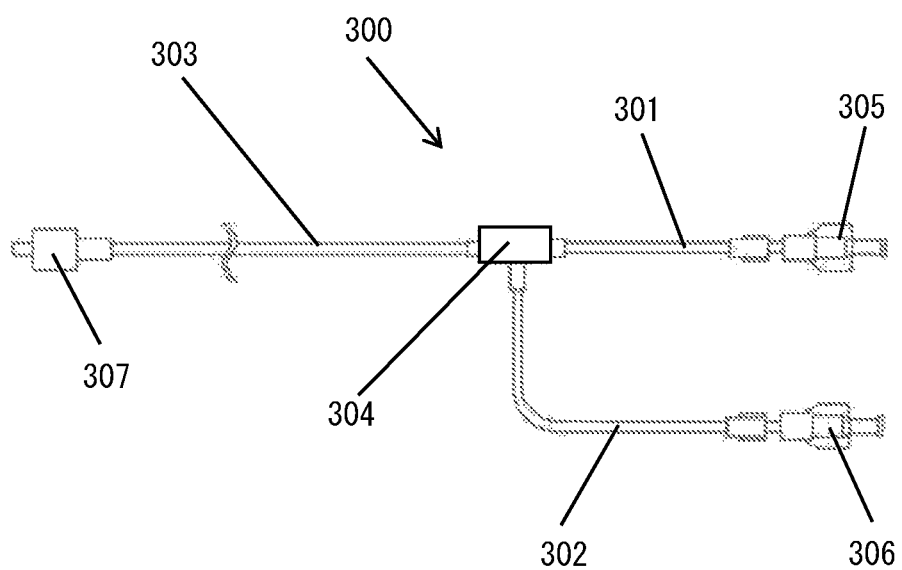
FIG. 4 is a view showing an embodiment of an extension tube connected to a syringe.

As the piston 222 moves toward the front of the cylinder 221, the filled chemical liquid is pushed out from the syringe 220 through the nozzle portion 221b. For example, an extension tube 300 as shown in FIG. 4 that constitutes the extracorporeal circuit portion of the injection circuit can be connected to the front of each syringe 220. The extension tube 300 has a first tube 301, a second tube 302, a third tube 303 and a T-shaped connector 304 for connecting them, and takes the form of a branch tube branched at the rear side as a whole. The first tube 301 and the second tube 302 have connectors 305 and 306 at their ends for connection with the nozzle portion 211b of the syringe 220, respectively. The third tube 303 has a connector 307 for connection with a catheter or the like at the front end thereof.

At least one of the connectors 305 and 306 connected to the first tube 301 and the second tube 302 may include a one-way valve. The one-way valve has a valve body that is actuated by a back pressure of a fluid to close a flow path, and functions to prevent backflow of the fluid from the front end to the rear end of the extension tube 300, that is, a side to which the catheter or the like is connected to a side to which the syringe 220 is connected. Further, at least one of the one-way valves may have a release function that can arbitrarily hold the valve body at the open position of the flow path by a predetermined operation. Since the wan-way valve has a release function, it is possible not only to prevent blood from flowing backward to the syringe 220 side, but also to introduce blood in order to confirm whether the front end of the catheter or the like is normally located in the blood vessel of the patient, that is a rout check.

In a state where the extension tube 300 is connected to the two sets of syringe assemblies 200, the end of the intracorporeal circuit portion such as a catheter inserted into the blood vessel of the patient is connected to the third tube 303. Then, it will be in a state which can inject the chemical liquid to the patient. As the chemical liquid to be filled in the syringe 220, for example, a contrast medium can be filled in the syringe 220 connected to the first tube 301, and a physiological saline can be filled in the syringe 220 connected to the second tube 302. Alternatively, syringes 220 filled with contrast agents having different concentrations may be connected to the first tube 301 and the second tube 302, respectively.

A contrast medium used for imaging a medical image has a relatively high viscosity, and in particular, a contrast medium used for imaging an image with an angiography apparatus tends to have a higher viscosity than other types of contrast mediums. Moreover, the catheter is generally very thin with an inner diameter of less than 2 mm. Therefore, when the contrast medium is filled in the syringe 220 as a chemical liquid and the piston 222 is advanced to inject the contrast medium, a very high internal pressure is generated in the cylinder 221. This high internal pressure may cause the cylinder 221 to expand and cause various troubles in injection of the contrast medium.

The protective cover 270 suppresses expansion and breakage due to an increase in the internal pressure of the cylinder 221 during the injection of the chemical liquid, and is a cylindrical member dimensioned so that there is almost no gap between the outer periphery of the cylinder 221 when the cylinder 221 is inserted. In order for the protective cover 270 to perform this function, it is preferable that the protective cover 270 is formed with a thickness having a mechanical strength that can sufficiently withstand the internal pressure acting on the cylinder 221 during the injection of the chemical liquid.

An opening through which the nozzle portion 221b of the syringe 220 passes is formed at the front end of the protective cover 270. The syringe 220 is held in a state where the nozzle portion 221b protrudes from the opening. A cover flange 271 is formed at the rear end of the protective cover 270, and a ring-shaped recess for receiving the flange 221a of the cylinder 221 is formed at the end surface of the cover flange 270.

The injection head 110 includes first and second piston driving mechanisms 130a and 130b (see FIG. 1) are arranged corresponding to the position where each syringe assembly 200 is mounted. The piston driving mechanism are independently driven to move the pistons 222 of the two sets of syringe assemblies 200 mounted on the injection head forward and backward. Each of the piston drive mechanisms 130a and 130b includes a presser 131 that holds a convex portion formed at the rear end of the piston 222, a drive source such as a motor that moves the presser 131 forward and backward, and a power transmission mechanism that connects them.

The syringe assemblies 200 mounted on the injection head 110 can inject the chemical liquids filled in the syringes 220 into the patient separately or simultaneously by moving the piston 222 forward by the piston driving mechanisms 130a and 130b. As the piston drive mechanism 130, a known mechanism generally used in this type of injection device can be employed.

At the front end portion of the injection head 110, there are provided a syringe receiver 120 and a clamper 140 that constitute a syringe mounting portion on which the syringe assembly 200 is placed. The syringe receiver 120 is located on a front side of the clamper 140 and has two recesses 121 so as to receive the outer periphery of each syringe assembly 200 individually. The clamper 140 is supported so as to be openable and closable with respect to the syringe receiver 120, and is configured to individually hold the cover flange 271 of the protective cover 270 of each syringe assembly 200. Each syringe assembly 200 is positioned in the recess 121 with the nozzle portion 221b facing the front end side, and the syringe assembly 200 is fixed to the injection head 110 by closing the clamper 140.

In the present invention, the protective cover 270 is not an essential element, and the syringe 220 may be directly mounted on the injection head 110. That is, the present invention includes both an aspect in which the syringe 220 is directly mounted on the injection head 110 and an aspect in which the syringe 220 is indirectly mounted via another member.

The injection head 110 can have an exterior cover 125 that covers substantially the entire mechanism except for the portion including the syringe receiver 120 and the clamper 140. In this case, the exterior cover 125 can have a mark 125a for distinguishing the corresponding presser 131 at a position corresponding to each presser 131. The mark 125a may be any character or symbol, and in this embodiment, the characters "A" and "B" are used. This mark can also be used to distinguish the syringe 220 (chemical liquid) on an injection condition setting screen 400 (see FIG. 5) described later. In the following description, the chemical liquids filled in the syringes 220 mounted on the syringe receiver 120 may be referred to as "chemical liquid A" and "chemical liquid B" corresponding to the mark 125a.

Referring to FIG. 2 again, the chemical liquid injector 100 may further include a hand switch 118 and/or a foot switch 119 as an option. The hand switch 118 has an operation button, and can be used to control the start and stop of the injection operation so that the injection operation of the chemical liquid by the injection head 110 is performed only while the operation button is pressed. The foot switch 119 can be used to control the start and stop of the injection operation so that the injection operation of the chemical liquid by the injection head 110 is performed only while the foot switch 119 is stepped on, for example, when performing test injection.

"Test injection" is an injection of a chemical liquid performed as necessary prior to imaging for obtaining a medical image in order to identify individual differences in contrast effects and/or to confirm the tip position of the injection circuit. The injection of the chemical liquid for obtaining the medical image may be referred to as "main injection" for the purpose of distinction from the test injection. In the test injection, a smaller volume of chemical liquid is usually injected than in the main injection. In addition, the flow rate of the chemical liquid in the test injection is usually predetermined or set to be the same as the flow rate of the chemical liquid in the main injection. This test injection can also be performed by operating the hand switch 118. In this case, the main injection can be performed when the hand switch 118 is operated after the setting of the chemical injection protocol is completed and the preparation for injection is completed (standby state), and the test injection can be performed when the hand switch 118 is operated before the standby state.

Next, an example of a procedure for injecting a chemical liquid using the above-described diagnostic imaging system will be described.

First, the power supply of the chemical liquid injector 100 is turned on by an operator. Thereafter, the syringe assembly 200 filled with a chemical liquid to be injected into the patient is mounted on the injection head 110. Alternatively, the syringe assembly 200 filled with the chemical liquid may be mounted on the injection head 110 By connecting a chemical liquid container (not shown) to the nozzle portion 221b via an appropriate tube after mounting an empty syringe assembly 200 that is not filled with the chemical liquid to the injection head 110, moving the piston 222 backward by the piston drive mechanism in this state, and filling the syringe assembly 200 with a chemical solution. As for the syringe 220 constituting a part of the syringe assembly 200, in this specification, a syringe, such as the former, filled with a chemical liquid by a manufacturer is called a p refilled type, and a syringe, such as the latter, filled with a chemical liquid in a medical field is also called a post-filling type.

The syringe assembly 200 can be mounted on the injection head 110 by the following procedure, for example. First, with the clamper 140 in the open position, the operator places the syringe assembly 200 on the recess 121 of the syringe receiver 120. At this time, the convex portion of the piston 222 at the rear end position is held by the presser 131. When the syringe assembly 200 is placed on the recess 121, the operator closes the clamper 140, whereby the syringe assembly 200 is held on the injection head 110.

The injection head 110 preferably has a lock mechanism (not shown) for releasably locking the clamper 140 in the closed position. The lock mechanism may be any mechanism as long as it can lock and release the clamper 140 in the closed position. By having the locking mechanism, it is possible to prevent the syringe assembly 200 attached to the injection head 110 from being detached from the injection head 110.

The injection head 110 preferably comprises at least one sensor which detects that the syringe assembly 200 is mounted on the injection head 110. The fact that the syringe assembly 200 is mounted on the injection head 110 can be detected, for example, by a first sensor which detects that the syringe assembly 200 is placed on the syringe receiving recess 121 and a second sensor which detects that the clamper 140 is in the closed position. A sensor that can be used as the first sensor is, for example, a sensor that is disposed in the syringe receiving recess 121 and can detect the syringe assembly 200 in the syringe receiving recess 121. A sensor that can be used as the second detector is, for example, a sensor that is built in the injection head 110 and can detect the tip of the clamper 140 when the clamper 140 is in the closed position.

These sensors may be sensors which can detect an object to be detected, such as the syringe assembly 200, the clamper 140, when the distance between the object to be detected and the sensor becomes a predetermined distance or less (including contact). Specifically, usable sensors include an optical sensor that optically detects the presence or absence of an object in the detection region, a proximity sensor that detects the presence or absence and position of an object by detecting magnetism as a detection medium, and a mechanical switch that turns on/off by the contact/non-contact of the object to be detected. The injection head 110 does not need to include both the first sensor and the second sensor in order to detect that the syringe assembly 200 is mounted on the injection head 110, and may have one of the sensors.

As described above, by making it possible to detect that the syringe assembly 200 is mounted on the injection head 110, for example, the injection control unit 101 can cause the display unit 104 to display information indicating that the mounting of the syringe assembly 200 has been completed to visually notify the operator, and can move the operation of the chemical injection device 100 to the next step.

At this time, the information displayed on the display unit 104 may be a message by characters or information represented by symbols. Alternatively, a light emitting lamp (not shown) is provided separately from the display unit 104, and the injection control unit 101 can also turn on the light-emitting lamp to visually notify the operator that the mounting of the syringe assembly 200 is completed. In this case, the light emitting lamp can be provided in the injection head 110. The position of the light emitting lamp in the injection head 110 may be arbitrary, but the position is preferably in the vicinity of the part that the operator operates last when mounting the syringe assembly 200, for example, in the vicinity of the clamper 140. In particular, as shown in FIG. 3, in the case where the injection head 110 has the marks 125a (specifically, the letters "A" and "B") to allow the two piston drive mechanisms 130a, 130b to be identified, It is preferable to arrange two light-emitting lamps so that these mark portions each emit light as a light-emitting portion. The color visually recognized by the lighting of the light-emitting lamp may be arbitrary, and may be a different color for each corresponding chemical solution, for example, blue and green. The injection head 110 may further include a light emitting unit 126 that emits light in the above-described standby state by turning on another light emitting lamp. In the form shown in FIG. 3, a plurality of light emitting units 126 are arranged at positions separated from each other, whereby it can be visually recognized from any direction that the injection head is in the standby state.

After mounting the syringe assembly 200 to the injection head 110 is completed as described above, the injection control unit 101 performs an operation for injecting the chemical liquid. This operation can include, for example, the following series of steps.

(1) Receiving Data Input and Setting Injection Conditions
(2) Performing Injection Operation According to Set Injection Conditions
(3) Injection Operation End Processing These processes will be described in order below.
(1) Receiving Data Input and Setting Injection Conditions In this step, the injection control unit 101 displays a screen for setting injection conditions on the display unit 104 and receives an input for setting injection conditions from the input unit 103. When the display unit 104 and the input unit 103 constitute a touch panel, the injection control unit 101 can display an injection condition setting screen 400 including an icon for receiving data input on the touch panel.

Figure 5:
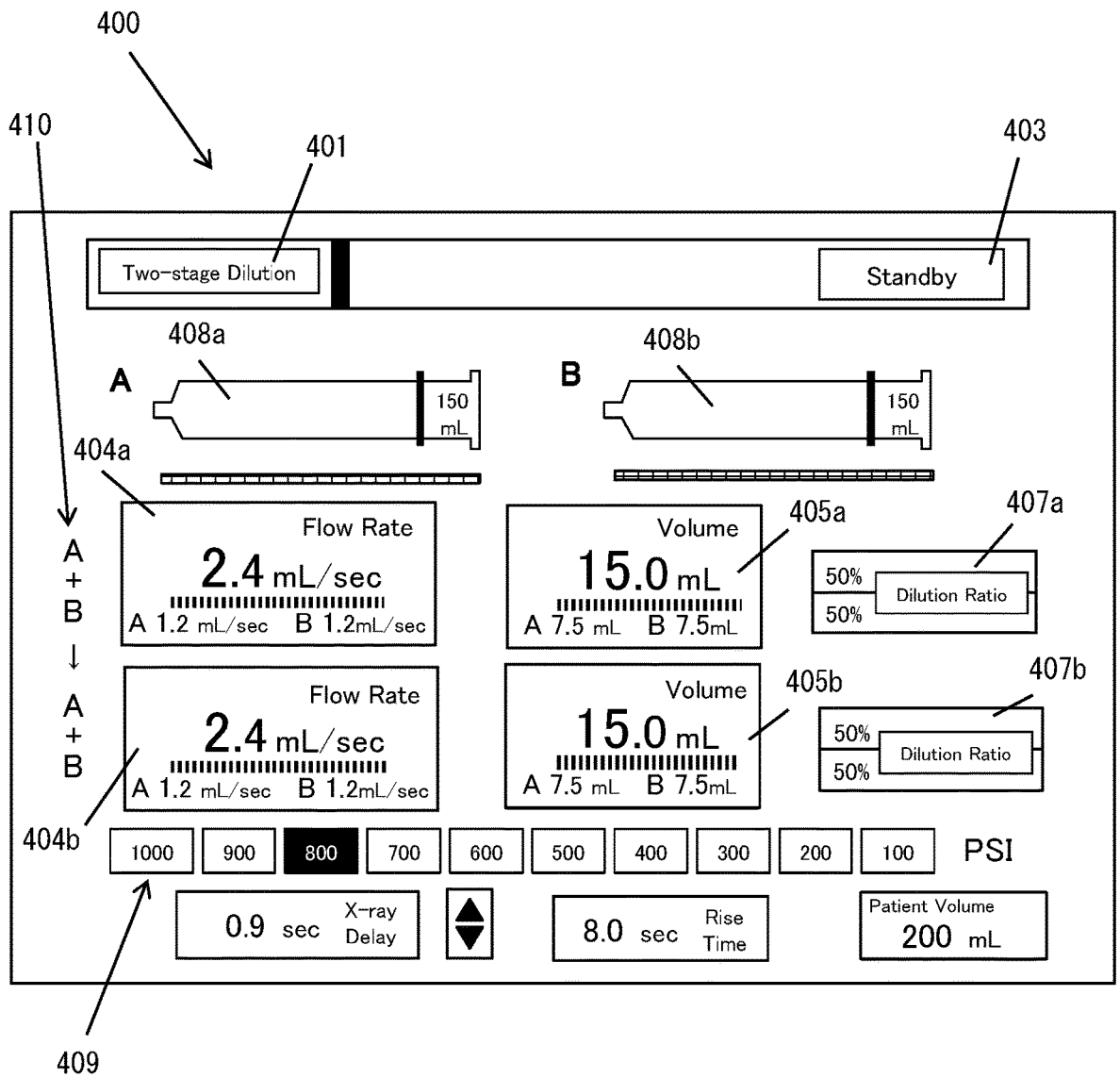
FIG. 5 is a diagram showing an example of an injection condition setting screen displayed when setting injection conditions in an embodiment of the present invention.

An example of the injection condition setting screen 400 is shown in FIG. 5. FIG. 5 shows an injection condition setting screen 400 in the two-stage injection mode which is one of one or a plurality of injection modes set in the injection control unit 101, and the injection condition setting screen 400 can include injection mode icon 401, confirmation icon 403, flow rate setting icons 404a and 404b, injection volume setting icons 405a and 405b, chemical liquid mixing ratio setting icons 407a and 407b, syringe information icons 408a and 408b, injection pressure limit value setting icon 409, etc.

The syringe information icons 408a and 408b graphically display information on the syringes 220 for the chemical liquid A and the chemical liquid B that are mounted on the injection head 110 (see FIG. 3). The information displayed on the syringe information icons 408a and 408b can include the volume of the chemical liquid filled in the mounted syringe 220. During the injection operation of the chemical liquid, it is also possible to allow the operator to visually recognize the chemical liquid injection operation by displaying an arbitrary animation on the injection condition setting screen 400 or on another screen.

The injection mode icon 401 is an icon representing which injection mode is performed among one or a plurality of injection modes set in the injection control unit 101. The injection mode includes, for example, "normal injection mode" in which the injection is performed only with the chemical liquid A, "flash mode" in which the chemical liquid B is injected after the injection of the chemical liquid A is completed, "multiple mode" in which only the chemical liquid A is injected in a plurality of phases, "two-stage injection mode" in which the chemical liquid A and the chemical liquid B are mixed at an arbitrary ratio and the second phase is performed after the first phase and the like. FIG. 5 shows a state where the "two-stage injection mode" is selected. When the operator taps the injection mode icon 401, the injection control unit 101 switches the display of the injection mode icon 401, thereby switching the injection mode.

In FIG. 5, "two-stage dilution" is displayed on the injection mode icon 401 in which "two-stage injection mode" is selected, but the display is not limited to this as long as the user clearly recognizes that the display is "two-stage injection mode".

The injection mode set in the injection control unit 101 may be set in advance, or may be additionally set later by implementation of a program or the like.

The confirmation icon 403 is operated when the operator approves the injection condition displayed on the injection condition setting screen 400. When the confirmation icon 403 is tapped, the injection control unit 101 sets the chemical liquid injector 100 to the standby state, and the chemical liquid injection procedure can be shifted to the next step.

The injection pressure limit value setting icon 409 is an icon used for setting and inputting the injection pressure limit value of the chemical liquid in the first phase and the second phase. In this embodiment, when the operator selects one of the displayed values by tapping, the selected injection pressure limit value is set in the injection control unit 101. When the injection pressure limit value is set, the injection control unit 101 controls the operation of the piston driving mechanisms 130a and 130b so as not to exceed the set injection pressure limit value. The detection of the injection pressure will be described later.

The flow rate setting icons 404a and 404b and the injection volume setting icons 405a and 405b are used for setting and inputting the flow rate and the injection volume of the chemical liquid A and the chemical liquid B for the first phase and the second phase, respectively. In the injection condition setting screen 400 shown in FIG. 5, the flow rate setting icon 404a and the injection volume setting icon 405a on the upper part are icons for the first phase, and the flow rate setting icon 404b and the injection volume setting icon 405b on the lower part are icons for the second phase.

The setting of the flow rate and the setting of the injection volume can be performed as follows. In setting the flow rate, for example, when the operator taps the flow rate setting icons 404a and 403b, the injection control unit 101 displays a numeric keypad icon (not shown) for inputting the flow rate superimposed on the injection condition setting screen 400. The injection volume can also be set in the same manner as the setting of the flow rate. The numeric keypad icon may be the same as a numeric keypad icon 431 (see FIG. 6) on a ratio setting screen 430 described later, for example. In the "two-stage injection mode", the total flow rate and the total injection volume of the chemical liquid A and the chemical liquid B is set by using the flow rate setting icons 404a and 404b and the injection volume setting icons 405a and 405b. On the flow rate setting icons 404a and 404b and the injection volume setting icons 405a and 405b, it can be displayed the flow rate and injection volume of the chemical liquid A and the flow rate and injection speed of the chemical liquid B according to the mixing ratio set in the chemical liquid mixing ratio setting icons 407a and 407b, respectively, in addition to the total flow rate and the total injection volume of the chemical liquid A and the chemical liquid B, The chemical liquid mixture ratio setting icons 407a and 407b are icons used for setting and inputting the mixing ratio of the chemical liquid A and the chemical liquid B of the chemical liquid injected in each of the first phase and the second phase. There are several ways of expressing the mixing ratio of the chemical liquid. In this embodiment, the mixing ratio of the chemical liquid is represented by the volume of the chemical liquid A relative to the total volume of the chemical liquid A and the chemical liquid B, that is, the mixing ratio calculated by the volume of the chemical liquid A/(the volume of the chemical liquid A+the volume of the chemical liquid B). This means that, for example, when the chemical liquid A is a contrast medium and the chemical liquid B is a physiological saline, how much the contrast agent is included in the total volume. For example, the mixing ratio may be set to 50% as a default value. With the chemical liquid mixture ratio setting icons 407a and 407b of this embodiment, the mixing ratio can be set within a range of 0% to 100%. When the mixing ratio is 0%, only the chemical liquid A is injected, and when the mixing ratio is 100%, only the chemical liquid B is injected. In the injection condition setting screen 400 shown in FIG. 5, the chemical liquid mixture ratio setting icon 407a on the upper part is an icon for the first phase, and the chemical liquid mixture ratio setting icon 407b on the lower part is an icon for the second phase.

Although the case where the chemical liquid A is a contrast medium and the chemical liquid B is a physiological saline has been described above, the chemical liquid A may be a physiological saline and the chemical liquid B may be a contrast medium. In this case, the mixing ratio means how much physiological saline is included with respect to the total volume.

The mixing ratio can be set as follows, for example.

Figure 6:
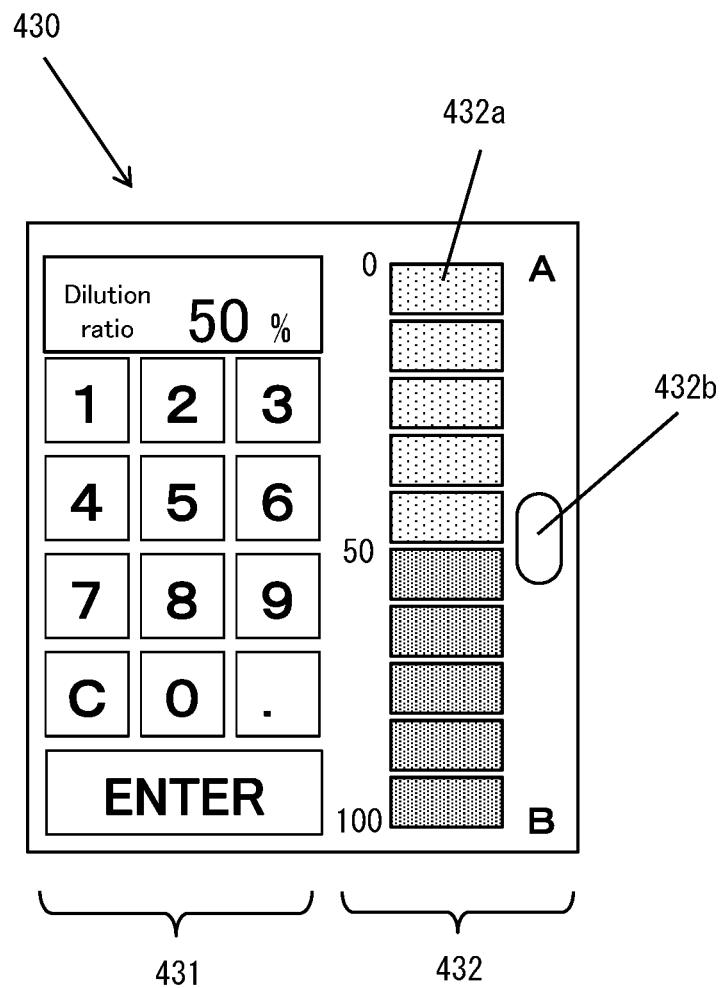
FIG. 6 is a diagram showing an example of a screen displayed when the mixing ratio is changed on the injection condition setting screen shown in FIG. 5.

When the operator taps the chemical liquid mixture ratio setting icons 407a and 407b, the injection control unit 101 displays a mixture ratio input screen 430 as shown in FIG. 6, which is one embodiment of the mixture ratio input screen, as a pop-up screen on the injection condition setting screen 400, or switches the display from the injection condition setting screen 400 to the mixing ratio input screen 430. The mixing ratio input screen 430 can include a numeric keypad icon 431 and a ratio setting bar 432. With the numeric keypad icon 431, the ratio of the volume of the chemical liquid A to the total volume of the chemical liquid A and the chemical liquid B can be set numerically. When the operator operates the numeric keypad icon 431 to input a numerical value, the injection control unit 101 determines the input numerical value as a mixing ratio.

On the other hand, the ratio setting bar 432 may include a ratio displaying portion 432a and a slider icon 432b. The ratio displaying portion 432a indicates the ratio between the chemical solution A and the chemical solution B as a band graph, and the slider icon 432b is controlled its display position such that the slider icon 432b can be moved along the ratio displaying portion 432a while being touched by the operator. When the position of the slider icon 432b is moved by the operation of the operator, the injection control unit 101 sets the mixing ratio to a ratio corresponding to the position of the slider icon 432b. In order to make it easy for the operator to visually recognize the mixing ratio, the ratio displaying portion 432a may display the chemical liquid A side and the chemical liquid B side in different colors with respect to the position of the slider icon 432b.

The mixing ratio can be set using either the numeric keypad icon 431 or the ratio bar 432. Further, the mixture ratio input screen 430 may have only one of the numeric keypad icon 431 and the ratio bar 432. Furthermore, the input of the mixing ratio is not limited to the above method, and any method can be used.

When the mixing ratio is set, the injection control unit 101 displays the set mixing ratio on the mixing ratio icons 407a and 407b on the injection condition setting screen 400 by deleting the pop-up of the mixing ratio input screen 430 from the injection condition setting screen 400 or switching the display to the injection condition setting screen 400 depending on the display form of the mixing ratio input screen 430. In addition, in case that the flow rate setting icons 404a and 404b and the injection volume setting icons 405a and 405b include the display of the respective flow rates and injection volumes of the chemical liquid A and the chemical liquid B, these displays are also changed to the values of the flow rate and the injection volume according to the set mixing ratio.

The injection condition setting screen 400 can include an injection pattern displaying portion 410. On the injection pattern displaying portion 410, an injection pattern of the chemical liquid to be injected according to the mixing ratio of the chemical liquid A and the chemical liquid B set in the first phase and the second phase is displayed. The display form of the injection pattern on the injection pattern displaying portion 410 is arbitrary. In the example shown in FIG. 5, the upper part and the lower part of the arrow represent the injection in the first phase and the second phase, respectively. "A+B" in each phase means that the chemical liquid A and the chemical liquid B are injected simultaneously.

Examples of injection patterns that can be set in the two-stage injection mode are shown below.

"A+B→A+B"     (a)

It is an injection pattern when the mixing ratio of the chemical liquid A and the chemical liquid B is set to other than 0 in both the first phase and the second phase.

"A→A+B"     (b)

It is an injection pattern when the mixing ratio of the chemical liquid B is set to 0 in the first phase, and the mixing ratio of the chemical liquid A and the chemical liquid B is set to other than 0 in the second phase.

"A+B→A"     (c)

It is an injection pattern when the mixing ratio of the chemical liquid A and the chemical liquid B is set to other than 0 in the first phase, and the mixing ratio of the chemical liquid B is set to 0 in the second phase.

"A+B→B"  (d)

It is an injection pattern when the mixing ratio of the chemical liquid A and the chemical liquid B is set to other than 0 in the first phase, and the mixing ratio of the chemical liquid A is set to 0 in the second phase.

"B→A (or A+B)"  (e)

It is an injection pattern when the mixing ratio of the chemical liquid A is set to 0 in the first phase and the mixing ratio of the chemical liquid A is set to other than 0 in the second phase.

The injection patterns as described above can be appropriately used depending on the imaging region, the imaging purpose, and the like. The effectiveness of some of the injection patterns when the chemical liquid A is contrast medium and the chemical liquid B is physiological saline will be described below.

For example, in the injection pattern (b) "A→A+B", the contrast medium that is not diluted is injected in the first phase, and the contrast medium having a low concentration diluted with physiological saline is injected in the subsequent second phase. As a result, the blood vessel into which the contrast medium is injected has a higher contrast effect in the portion injected in the first phase than in the portion injected in the second phase. Such an injection pattern is suitable for imaging a blood vessel when the distal end portion is thin and difficult to be imaged, such as hepatic arteriography for example. By making the concentration of the contrast medium injected in the second phase lower than the concentration of the contrast medium injected in the first phase, there is a high concentration of contrast medium on the distal end portion that is difficult to be imaged, and there is a low concentration of the contrast medium at the proximal end portion where artifacts tend to be large. As a result, a good blood vessel image can be obtained from the proximal end portion to the distal end portion.

In addition, in the injection pattern (c) "A+B→A", a contrast medium diluted with physiological saline is injected in the first phase, and a contrast medium that is not diluted is injected in the second phase. As a result, the blood vessel into which the contrast medium is injected has a higher contrast effect in the portion injected in the second phase than in the portion injected in the first phase. Such an injection pattern is suitable for imaging a blood vessel when it is desired to distinguish between an artery and a vein in order to know the malformed region in a cerebral artery malformation examination, for example. By making the concentration of the contrast agent injected in the first phase lower than the concentration of the contrast agent injected in the second phase, when most of the contrast agent injected in the first phase reaches the vein, most of the contrast agent injected in the second phase will be in the artery. As a result, it is possible to distinguish between an artery and a vein by a difference in contrast between blood vessel images caused by a difference in contrast agent concentration between the artery and the vein.

In the injection pattern (e) "B→A (or A+B)", physiological saline is injected in the first phase, and undiluted or diluted contrast medium is injected in the second phase. The injection volume of the chemical liquid B injected in the first phase in the injection pattern (e) is preferably an volume at which at least the extracorporeal circuit portion and the intracorporeal circuit portion are filled with the chemical liquid B, for example, 3 to 6 ml. Thereby, the contrast medium is injected in a state where the portion of the blood vessel downstream from the injection circuit is filled with the physiological saline. The implantation pattern (e) has the following effects, for example.

(i) Since the physiological saline is less viscous than the contrast medium and blood, the contrast agent injected into a portion of a blood vessel filled with the physiological saline is likely to diffuse and penetrate into the blood vessel as compared to when injected into a portion of the blood vessel filled with blood. As a result, the contrast enhancement effect can be expected by injecting the physiological saline before injecting the contrast medium.

(ii) By injecting the physiological saline before injecting the contrast medium, the injection circuit and the blood vessel portion downstream of the contrast medium are flushed with the physiological saline. Thereby, even if the contrast medium remains in the injection circuit by the previous injection, it is possible to inject the contrast medium in a desired mixing ratio without being affected by the contrast medium remaining in the injection circuit. In this case, since the physiological saline is injected prior to the injection of the contrast medium, there is a delay in the time for the contrast medium to reach a desired region after the start of the injection. However, by setting a delay time according to the injection volume of the physiological saline, and performing the imaging operation after the set delay time elapses, it is possible to cancel the deviation in arrival time.

(iii) When injecting the contrast medium diluted with the physiological saline, if the ratio of the physiological saline and the contrast medium is extremely different, there is a possibility that both are not sufficiently mixed at the initial stage of mixing. Therefore, the physiological saline is injected before injecting the diluted contrast medium. Thus, the contrast medium can be injected into the body in a sufficiently mixed state with the physiological saline.

(iv) When generating a medical image, a subtraction process may be performed. In the subtraction process, blood vessel image data generated by extracting only blood vessel images is obtained by the difference processing between the plain image data obtained by imaging before injecting the contrast medium and the contrast image data obtained by imaging after injecting the contrast medium. At this time, if there is a displacement of the blood vessel between the plane image data and the contrast image data, accurate blood vessel image data cannot be obtained. It is considered that the displacement of the blood vessel is affected by the flow state of the liquid (blood, contrast medium, physiological saline, etc.) inside the blood vessel. Therefore, an imaging for obtaining the plain image data is performed during the physiological saline injected in the first phase flows in the blood vessel and an imaging for obtaining the contrast image data is performed during the contrast medium injected in the second phase flows in the blood vessel. Thus, the plane image data and the contrast image data can be obtained under almost the same conditions in which fluid flows in the blood vessel. As a result, the displacement of the blood vessel between these two image data is suppressed, and better blood vessel image data can be obtained. Therefore, the injection pattern (e) is considered to be effective in the subtraction process.

In the above, some examples of major injection patterns have been described. However, the present invention is not limited to the above-described injection patterns, and various injection patterns may be set as necessary.

The operator performs a data input operation as necessary in accordance with the display of the injection condition setting screen 400. When the input of all data for setting injection conditions is completed and the operator taps the confirmation icon 403, the display of the icon is switched to "start OK", and the chemical liquid injector 100 enters in a standby state in which the chemical liquid can be injected.

As described above, since the mixing ratio of the chemical liquids can be set in each of the first phase and the second phase, various injection patterns can be set according to the imaging region and purpose. Moreover, since various injection patterns can be set only in the two-stage injection mode without changing the injection mode, the setting operation including data input is extremely simple.

(2) Performing Injection Operation According to Set Injection Conditions

As described above, after the display is switched to "start OK" by tapping the confirmation icon 403, the hand switch 118 is operated, whereby the injection control unit 101 operates the piston driving mechanisms 130*a* and 130*b* to start the injection operation of the chemical liquid. The hand switch 118 may be a momentary operation type switch. In this case, the piston driving mechanisms 130*a* and 130*b* operate only while the button of the hand switch 118 is being pressed. The injection operation of the chemical liquid can also be started by a command from the diagnostic imaging apparatus 500 that is linked to the injector. For example, when an imaging operation start signal is transmitted from the diagnostic imaging apparatus 500 by an operation of the diagnostic imaging apparatus 500 by an operator and the imaging operation start signal is received by the injection control unit 101, then injection operation can be performed using the signal as a trigger.

The injection operation of the chemical liquid is performed by the injection control unit 101 controlling the operations of the piston driving mechanisms 130*a* and 130*b* so that the chemical liquid is injected under the set injection conditions (injection speed, injection volume, injection time, etc.). When the mixing ratio of the chemical liquid A and the chemical liquid B is other than 0, both the piston driving mechanisms 130*a* and 130*b* are operated simultaneously so that the chemical liquid A and the chemical liquid B are simultaneously injected at the set mixing ratio.

On the other hand, the diagnostic imaging apparatus 500 starts the imaging operation in response to the injection operation of the chemical liquid by the chemical liquid injector 100. The imaging operation by the diagnostic imaging apparatus 500 may be performed based on an operation of the diagnostic imaging apparatus 500 by an operator as a trigger, or may be automatically performed in conjunction with the injection operation by the chemical liquid injector 100. In case where the injection operation and the imaging operation are linked, the injection operation and the imaging operation can be controlled such that the imaging operation is started after a lapse of a predetermined time required for the injected chemical liquid to reach the target region after the start of the injection operation, for example, the injection control unit 101 of the chemical liquid injector 100 transmits an injection start signal to the imaging control unit 510 of the diagnostic imaging apparatus 500 simultaneously with the start of the injection operation, and the imaging control unit 510 that has received the injection start signal can control the imaging operation unit 520 to start the imaging operation after the predetermined time has elapsed; or the injection control unit 101 transmits an injection start signal to the imaging control unit 510 after the elapse of the predetermined time from the start of the injection operation, and the imaging control unit 510 controls the imaging operation unit 520 immediately after receiving the injection start signal to start the imaging operation.

The imaging control unit 510 can reconstruct the data obtained by the imaging operation of the imaging operation unit 520 to generate a medical image, and display the generated medical image on the display unit 504 in real time. Further, if the injection conditions such as the flow rate, the injection volume, the injection time, and the injection pressure of the chemical liquid are transmitted as data from the injection control unit 101 to the imaging control unit 510, the imaging control unit 510 can also display part or all of the injection conditions together with or separately from the medical images and the imaging conditions in real time to the display unit 503.

By displaying part or all of the injection conditions in real time, for example, when the imaging and the injection of the chemical liquid are repeated multiple times while changing the region in the examination and treatment of the liver, the cumulative injection volume and the cumulative X-ray irradiation volume up to the imaging stage can be displayed. As a result, it is determined immediately whether the cumulative X-ray irradiation dose does not exceed the reference value, and whether the injection volume of the contrast medium does not exceed the reference value for patients with poor liver function, the X-ray irradiation volume and injection volume of the contrast medium can be adjusted as necessary when the X-ray irradiation volume and/or the injection volume is likely to exceed the reference value.

(3) Injection Operation End Processing

After completion of the injection operation, the injection control unit 101 can display the injection result on the display unit 104 as one of the injection operation end processing. Examples of results to be displayed include at least one of an injection end date and time, an injection mode, a set imaging region, a flow rate, an injection volume, a mixing ratio, a time required for injection, a maximum pressure during injection and the like. In addition, as one of the injection operation end processing, the injection control unit 101 records these injection results in an appropriate memory device inside or outside the chemical liquid injector 100 or transmits them to the diagnostic imaging apparatus 500.

When the injection operation end processing is completed, the injection control unit 101 can display the injection condition setting screen 400 on the display unit 104 again by a predetermined operation by the operator. When the injection of the chemical liquid is repeated again under different conditions or the same conditions for the next examination or treatment, the injection conditions can be set on the injection condition setting screen 400, and the chemical liquid may be injected under the set injection conditions. In addition, when the injection of the chemical liquid is performed repeatedly, the injection conditions in each injection performed repeatedly can also be set previously. When the injection conditions for each injection are set previously, it is possible to start the next injection operation without displaying the injection condition setting screen 400 every time the injection is completed.

While the present invention has been described with reference to the exemplary embodiments, the present invention is not limited to the above-described embodiments.

Another Expression of Mixing Ratio

In the above-described embodiment, the mixing rate of the chemical solution is expressed as the mixing ratio.

However, the mixing rate can also be expressed as a dilution ratio. Also in this case, similar to the concept of the mixing ratio described above, the dilution ratio is calculated by the total volume of the chemical liquid A and the chemical liquid B with respect to the volume of the chemical liquid A, that is, (the volume of the chemical liquid A+the volume of the chemical liquid B)/the volume of the chemical liquid A. For example, in the case of chemical liquid A: chemical liquid B=1:1, it is 50% when expressed by the above-mentioned mixing ratio, but it is 2 times when expressed by the above dilution ratio. These represent the same mixing rate in different expression methods.

Figure 7A:
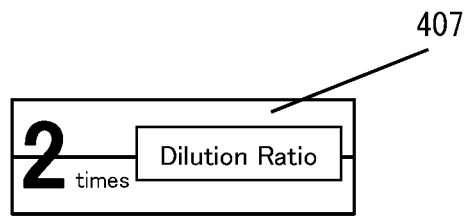
FIG. 7A is a diagram showing another example of a chemical liquid mixing ratio setting icon that can be displayed on the injection condition setting screen shown in FIG. 5.
Figure 7B:
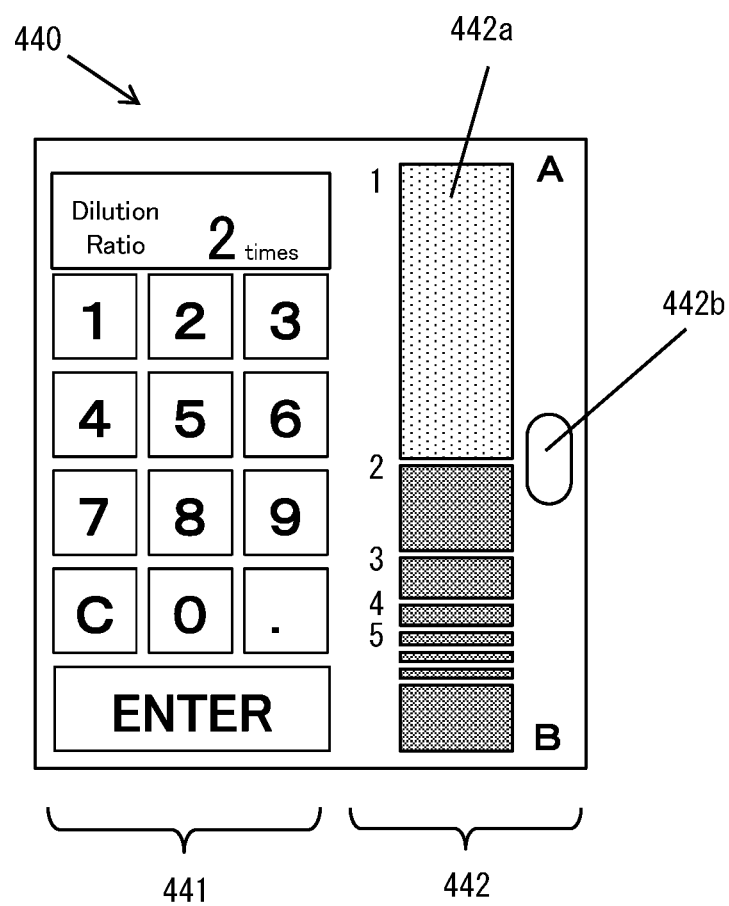
FIG. 7B is a diagram showing an example of a dilution ratio input screen that can be used when setting a dilution ratio as an example of the mixing ratio.

When the mixing rate is expressed by the dilution ratio, the injection condition setting screen and the like are changed as necessary. For example, as shown in FIG. 7A, the currently set dilution ratio is displayed on the chemical liquid mixing rate setting icon 407 displayed on the injection condition setting screen. In addition, when the operator taps the chemical liquid mixing rate setting icons 407a and 407b in order to change the mixing rate, the injection control unit 101 pops up a dilution ratio input screen 440, which is another form of the mixing rate input screen, as shown in for example FIG. 7B on the injection condition setting screen.

The dilution ratio input screen 440 can have at least one of a numeric keypad icon 441 and a ratio setting bar 442, as in the case with the mixing ratio input screen 430 shown in FIG. 6. With the numeric keypad icon 441, the dilution ratio represented by the total volume of the chemical liquid A and the chemical liquid B with respect to the volume of chemical solution A can be set numerically. When the operator operates the numeric keypad icon 441 to input a numerical value, the injection control unit 101 determines the input numerical value as the dilution ratio.

On the other hand, the ratio setting bar 442 can have a ratio displaying portion 442a and a slider icon 442b. As an example, the ratio displaying portion 442a can represent a set ratio in a logarithmic graph format. By displaying the ratio displaying portion 442a in a logarithmic graph, the operator can intuitively grasp the ratio between the chemical liquid A and the chemical liquid B. The position where the slider icon 442b is displayed is controlled such that the slider icon 442b can be moved along the ratio displaying portion 442a while being touched by the operator. When the position of the slider icon 442b is moved by the operator, the injection control unit 101 sets the dilution ratio to a ratio corresponding to the position of the slider icon 442b. In addition, similarly to the mixing ratio input screen 430, the chemical liquid A and the chemical liquid B may be displayed in different colors with respect to the position of the slider icon 442b.

Another Embodiment of Mixing Rate Setting Screen

Figure 7C:
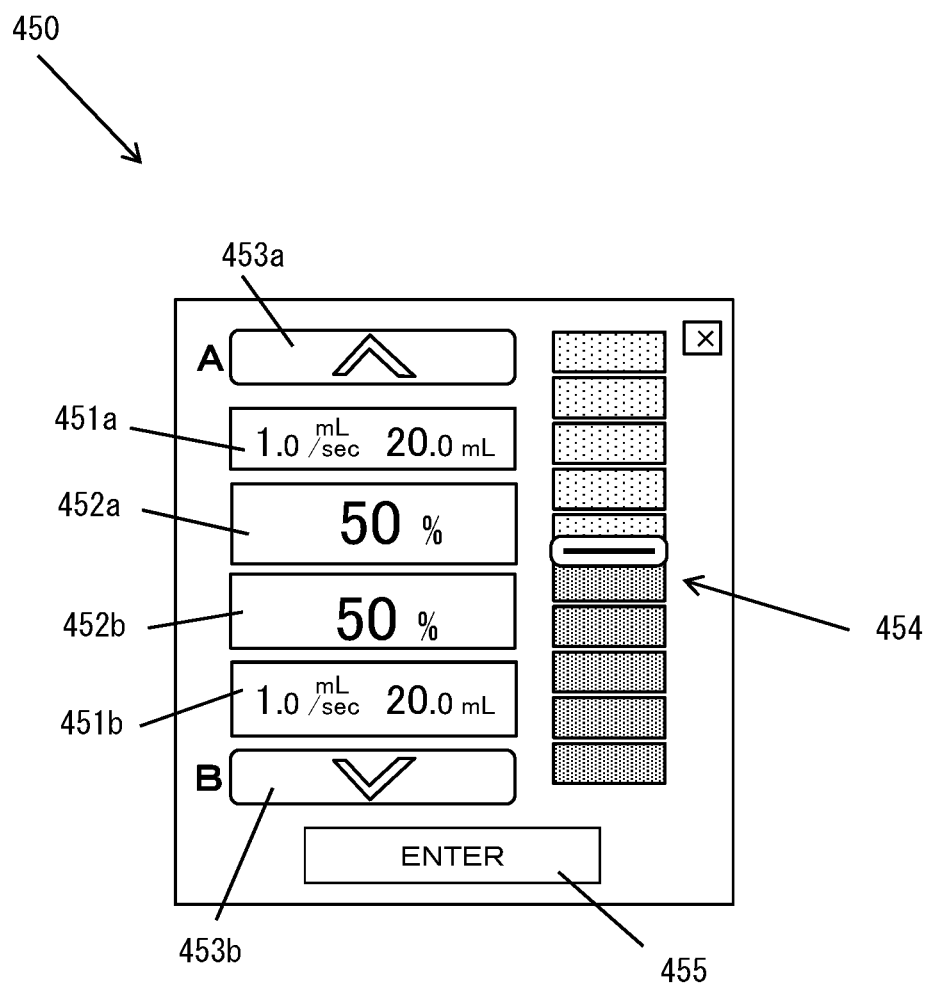
FIG. 7C is a diagram showing still another embodiment of the mixing ratio input screen.

FIG. 7C shows still another embodiment of the mixing rate input screen. The mixing rate input screen 450 shown in FIG. 7C has flow rate/injection volume displays 451a and 451b, mixing rate displays 452a and 452b, and mixing rate adjustment icons 453a and 453b for each of the chemical liquid A and the chemical liquid B. The mixing rate adjustment icons 453a and 453b are used to change the mixing rate of the chemical liquids, and can be displayed such that when each of the mixing rate adjustment icons 453a and 453b are tapped, the mixing rate display 452a or 452b for the tapped liquid increase by 1%, and the other mixing rate display 452a or 452b decreases by 1%. In addition, a slide bar icon 454 can be provided for a case where the mixing rate is greatly changed. The slide bar icon 454 can include, for example, a ratio display portion that displays a mixing ratio of the chemical liquid A and the chemical liquid B on a band graph, and a slider icon displayed thereon. The display of the mixing rate of the chemical liquid A and the chemical liquid B can be changed, for example, in units of 10% when the operator touches the slider icon and moves it to the chemical liquid A side or the chemical liquid B side. When the operator taps the enter icon 455 after completing the input of the mixing ratio in this way, the input mixing ratio is set in the injection control unit 101.

(Container and Driving Mechanism)

In the above-described embodiment, the case where the container filled with the chemical solution is a syringe has been described as an example. However, in the present invention, the container is not limited to a syringe, and may be a chemical liquid bottle or a chemical liquid bag. In that case, as the driving mechanism for allowing the chemical liquid to flow out of the container, a driving mechanism corresponding to the form of the container, such as a tube pump type driving mechanism, can be used.

(Multistage Injection Phase)

In the above-described embodiment, the two-stage injection having the first injection phase and the second injection phase as the injection mode has been described as an example. However, the injection mode may be a multistage injection mode in which a series of injection operations are performed in three or more injection phases. In this case, it is preferable that the injection control unit 101 displays icons set for each injection phase, such as a flow rate setting icon, an injection volume setting icon, and a chemical liquid mixing rate setting icon, on the same injection condition setting screen, and the injection conditions can be set on the same injection condition setting screen.

(Purge Operation)

A purge operation can be performed prior to the injection of the chemical liquid. The purge operation is performed after the extracorporeal circuit portion (for example, the extension tube) of the injection circuit is connected to the syringe assembly 200 and before the chemical liquid injection operation is started. In the purge operation, fluid containing air and chemical liquid in the extracorporeal circuit portion is released from the injection circuit by the chemical liquid in the syringe 220. In order to release the fluid in the extracorporeal circuit portion from the injection circuit, the purge operation is performed in a state where the distal end of the extracorporeal circuit portion is not connected to the proximal end of the intracorporeal circuit portion, or a three-way stopcock is interposed between the extracorporeal circuit portion and the intracorporeal circuit portion to switch the three-way stopcock such that the chemical liquid is released from a side tube connected to the remaining port of the three-way stopcock. The purge operation is basically performed to fill the extracorporeal circuit portion with the chemical liquid when the extracorporeal circuit portion is not filled with the chemical liquid, and need not be performed when the extension tube 300 is filled with the chemical liquid. However, if the mixing rate is changed, such as when the second injection is performed at a different mixing rate from the first injection, for example, it may be preferable to perform the purge operation even if the extracorporeal circuit portion is filled with the chemical liquid.

In order to perform the purge operation, for example, the injection head 110 may have a purge button 123 (see FIG. 3). Alternatively, a purge icon (not shown) can be displayed on the injection condition setting screen 400 shown in FIG. 5. Furthermore, it is possible to have both of these. When the operator depresses the purge button 123 or taps the purge icon, the injection control unit 101 performs the purge operation.

In the purge operation, the operations of the piston driving mechanisms 130a and 130b can be controlled so that both the chemical liquid A and the chemical liquid B are discharged from the syringe 220 at the same rate and volume. Alternatively, when the mixing rate of the chemical liquid A and the chemical liquid B is set, the operations of the piston driving mechanisms 130a and 130b can be controlled so that the chemical liquid A and the chemical liquid B are discharged from each syringe 220 at the set mixing rate. As a result, since the chemical liquid is already filled at a desired mixing rate in a distal side from a junction portion of the extracorporeal circuit portion (for example, a T-shaped connector 304 of the extension tube 300 shown in FIG. 4), the chemical liquid mixed at a desired mixing rate is injected as soon as the injection operation is started. Therefore, it is possible to minimize an unnecessary injection of the chemical liquid and a time lag until the mixing rate of injected chemical liquids reaches a desired rate, and as a result, a good image can be obtained in a smaller volume of the chemical liquids and in a shorter time.

(Mixed Injection Using Hand Switch and/or Foot Switch)

The hand switch 118 and the foot switch 119 shown in FIG. 2 are suitably used when performing a small amount of liquid injection operation. The injection operation of a small amount of chemical liquid is performed, for example, when performing the test injection described above and when the injection operation is performed so that air is not mixed into the injection circuit when the extracorporeal circuit portion (for example, the extension tube) and the intracorporeal circuit portion (for example, the catheter) is connected.

When performing the test injection, it is preferable that the injection conditions other than the injection volume are the same for the test injection and the main injection in order to make the effect (for example, contrast effect) of the chemical liquid injection equal to the subsequent main injection. Usually, the test injection using the hand switch 118 or the foot switch 119 is set so that an unmixed chemical liquid (for example, contrast medium) is injected. Therefore, when the injection conditions for the main injection performed thereafter are already set, it is preferable that the injection control unit 101 controls the operation of each unit so that the chemical liquid is injected at the same flow rate and mixing rate as the main injection.

Also, when performing an injection operation so that air is not trapped in the injection circuit when the extracorporeal circuit portion and the intracorporeal circuit portion are connected, an injection operation of a non-mixed chemical liquid (for example, a contrast medium) is usually performed. More specifically, the operator holds the connecting portions between the extracorporeal circuit portion and the intracorporeal circuit portion, and connects the extracorporeal circuit portion and the intracorporeal circuit portion in the state where the chemical liquid is injected by operating the foot switch 119. During the connecting, the chemical liquid overflows from the distal end of the extracorporeal circuit portion, and therefore, the extracorporeal circuit portion and the intracorporeal circuit portion can be connected without trapping air. At this time, if the mixing rate of the chemical liquid in the next injection is already set, the injection control unit 101 controls the operation of each unit so that the injection operation of the chemical liquid is performed at the set mixing rate.

Thereby, air can be prevented from being trapped into the injection circuit, and it is possible to suppress unnecessary consumption of the chemical liquid during the injection operation. In addition, by such an injection operation, it is possible to efficiently inject the chemical liquid having a desired mixing rate at the next injection, since at least the extracorporeal circuit portion is filled with the chemical liquid mixed at the mixing rate at the next injection.

(Arrangement of Unit and the Like)

In the above-described embodiment, the injection control unit 101 is included in the chemical liquid injector 100 and the imaging control unit 510 is included in the diagnostic imaging apparatus 500 as shown in FIG. 1. However, both the injection control unit 101 and the imaging control unit 510 may be included in the chemical liquid injector 100, or both the injection control unit 101 and the imaging control unit 510 may be included in the diagnostic imaging apparatus 500. Alternatively, both the injection control unit 101 and the imaging control unit 510 may be included in a programmable computer device (not shown) separate from the chemical liquid injector 100 and the diagnostic imaging apparatus 500. Thereby, it is not necessary for the chemical liquid injector 100 and the diagnostic imaging apparatus 500 to have individual consoles, and the input unit and the display unit of each control unit can be made common. As a result, the configuration of the entire system can be simplified.

Furthermore, a specific function of the injection control unit 101 can be incorporated in a unit different from the unit in which the remaining other functions are incorporated. For example, the injection condition determination (calculation) function can be incorporated into the imaging control unit 510 and the remaining other functions can be incorporated into the injection control unit 101. In this case, it is not necessary to input data common to the determination of the imaging condition and the determination of the injection condition to the chemical liquid injector 100 and the diagnostic imaging device 500 in duplicate. Data that is insufficient when determining the injection conditions may be input from the imaging control unit 510, or may be transmitted from the injection control unit 101 to the imaging control unit 510.

The function of the injection control unit 101 and the function of the imaging control unit 510 can be realized by using various hardware as required, but the main part is realized by the function of the CPU corresponding to the computer program.

The computer program can be implemented as a computer program for making a diagnostic imaging system including the chemical liquid injector 100, the diagnostic imaging apparatus 500, or the chemical liquid injector 100 and the diagnostic imaging apparatus 500 to execute at least a part of the above-described procedure, for example, receiving an input of a mixing rate of a first chemical liquid and a second chemical liquid for each of a first injection phase and a second injection phase in a two-stage injection mode, setting an injection condition for the first chemical liquid and the second chemical liquid so that the first chemical liquid and the second chemical liquid are injected at the mixing rate received previously, and controlling a operation of a first driving mechanism and a second driving mechanism according to the injection condition set previously.

In terms of structure, the injection head 110 and the console 112 shown in FIG. 2 can be integrally configured. When the injection head 110 and the console 112 are integrally configured, the console 112 is also arranged in the examination room. Since the hand switch 118 can be used to start and stop the injection operation, the operator can control the start and stop of the injection operation in the operation room by the hand switch 118.

In the embodiment described above, the two piston driving mechanisms 130a and 130b are mounted on the common injection head 110. However, the chemical liquid injector may have two injection heads each equipped with one piston driving mechanism, and at the time of injection, the injection control unit 101 links each injection head with each other to mix a plurality of chemical liquid.

(Other Possible Configurations for Chemical Liquid) Injector (i) Load Cell

The chemical liquid injector 100 may further include a load cell for detecting the injection pressure. The load cell can be provided in the presser 131 (see FIG. 3), for example. As shown in FIG. 3, in the case of having a plurality of pressers 131, at least one of them may have the load cell. The injection pressure can also be detected by measuring the motor current flowing in the motor that is the drive source of the piston driving mechanisms 130a and 130b. When the load acting on the presser 131 increases, the motor current increases according to the load. This is used for detecting the injection pressure using the motor current. The detection of the injection pressure may be either one of detection using the load cell and detection using the motor current, or both may be used in combination. When both are used together, the injection pressure is usually detected by the load cell, and the measurement of the injection pressure using the measurement result of the motor current can be used only when the load cell fails.

(ii) RFID Module

Figure 8:
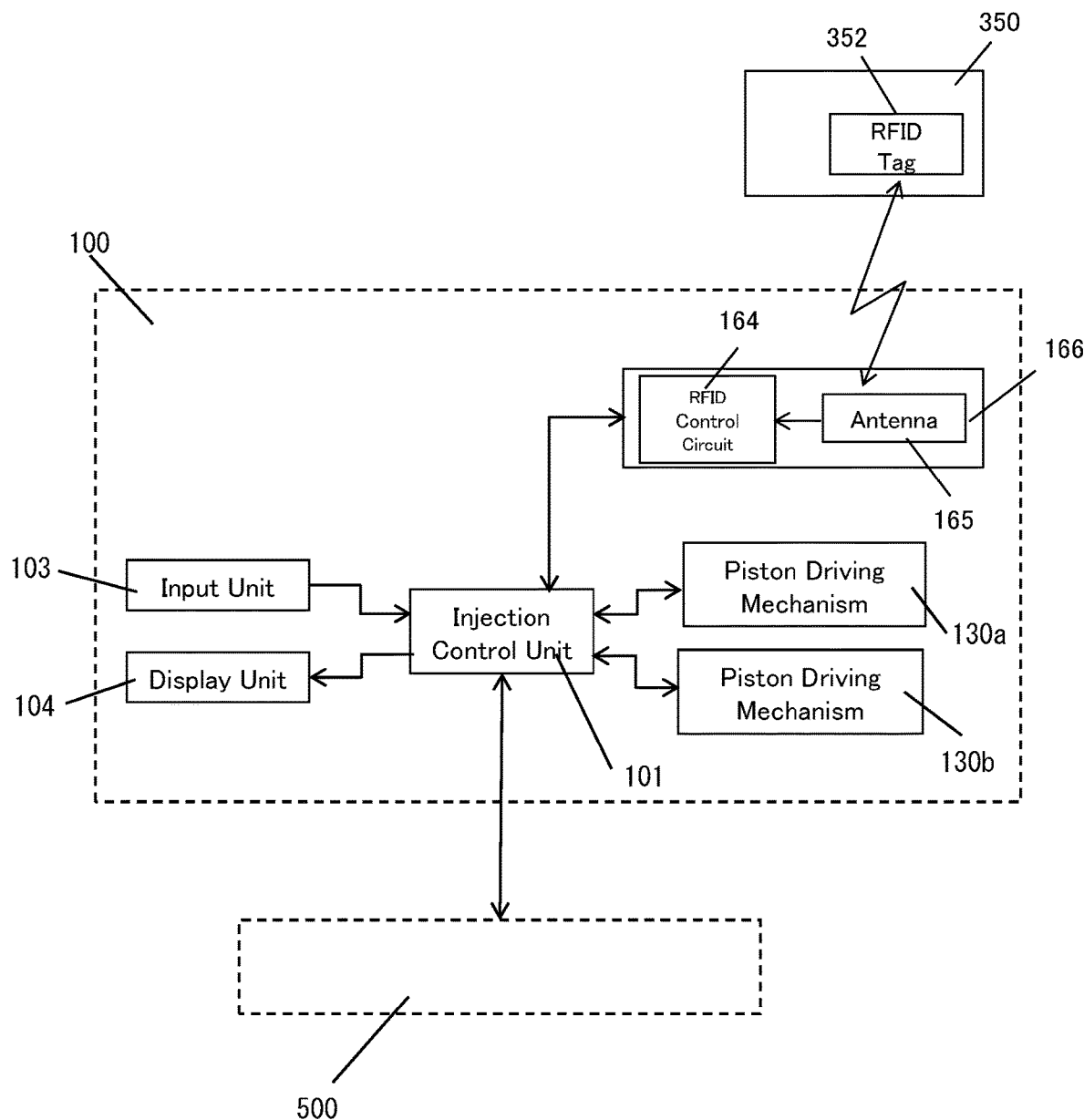
FIG. 8 is a schematic block diagram of a diagnostic imaging system in a case where the chemical liquid injector includes an RFID module.

As shown in FIG. 8, the chemical liquid injector 100 may further include an RFID module 166. Currently, some containers 350 containing chemical liquids, such as syringes and chemical liquid bottles, include an RFID tag 352 that is a data carrier in which information about the stored chemical liquid is recorded. The RFID tag 352 normally records information related to the stored chemical liquid. The RFID module 166 is for reading data from the RFID tag 352 and/or for recording data on the RFID tag 352. Since the chemical liquid injector 100 includes the RFID module 166, the data recorded on the RFID tag 352 can be used to control the operation of the chemical liquid injector 100 by the injection control unit 101. In FIG. 8, the same components as those shown in FIG. 1 are denoted by the same reference numerals as those in FIG. 1, and the description thereof is omitted here.

The RFID module 166 includes an RFID control circuit 164 and an antenna 165, and is configured to read the data recorded on the RFID tag 352 by the antenna 165, transmit the read data to the injection control unit 101, and/or record the data transmitted from the injection control unit 101 on the RFID tag 352. The RFID control circuit 164 controls the operation of the RFID module 166 for transmitting and receiving data. That is, the RFID module 166 functions as a reader that reads data from the RFID tag 352 or a reader/writer that also records data in the RFID tag.

In addition, the data can be automatically read from the RFID tag 352 when the container 350 containing the chemical liquid is appropriately mounted on the injection head 110 by arranging at least the antenna 165 of the RFID module 166 in the injection head 110 (see FIG. 2). Alternatively, for example, the RFID module may be a handy type unit different from the injection head 110, and the data is read from the RFID tag 352 when the operator brings the unit and the RFID tag 352 relatively close to each other.

Examples of data recorded on the RFID tag 352 include various data related to the chemical liquid stored in the container 350, such as a manufacturer, a type of a chemical liquid, a product number, a contained components (particularly, the iodine-containing concentration when the chemical liquid is a contrast medium), a volume of stored chemical liquid, lot number, expiry date and the like. When the container 350 is the syringe 220, examples of data include various data relating to the syringe 220, for example, a manufacturer, a unique identification number such as a product number, an allowable pressure value, a capacity of the syringe, a piston stroke, dimensions of necessary parts, a lot number and the like. At least a part of these data can be transmitted to the diagnostic imaging apparatus 500.

(iii) Voice Recognition Unit

The chemical liquid injector 100 can further include a voice recognition unit (not shown) as a data input interface. The voice recognition unit can include a microphone that obtains the voice generated by the operator and a voice recognition device that recognizes the voice obtained by the microphone and converts it into an operation signal for the chemical liquid injector 100. The location of the voice recognition device may be arbitrary, but the microphone is preferably located near the operator, for example, at or near the injection head 110.

Since the chemical liquid injector 100 includes the voice recognition unit, the operator can input and set the chemical liquid injection conditions without touching the injection head 110 and the console 112.

(Other Embodiments of Extension Tube)

The extension tube is preferably provided with a mixing device for appropriately mixing the contrast medium and the physiological saline. An example of an extension tube with a mixing device will be described with reference to FIGS. 9A, 9B and 9C.

The extension tube includes a first tube 231a which connects the syringe filled with the contrast medium and the mixing device 241, a second tube 231b which connects the syringe filled with the physiological saline and the mixing device 241, and a third tube 231c connected to a liquid outlet (detailed below) of the mixing device 241 and extending toward the patient. Although not particularly limited, the first and second tubes 231a and 231b may be connected to the conduit portion of the syringe via connectors 239a and 239b, respectively. Similarly, the third tube 231c may be connected to a catheter or the like via the connector 239c. As in the case of the extension tube 300 shown in FIG. 4, at least one of the connectors 239a and 239b connected to the first tube 231a and the second tube 231b may include one-way valve, and at least one of the one-way valves may have a release function.

Figure 9A:
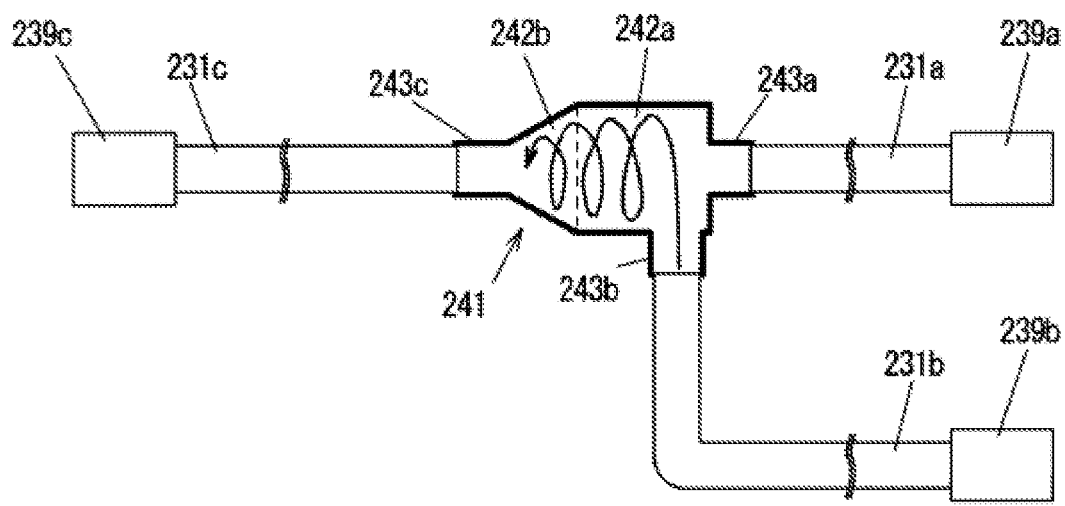
FIG. 9A is a diagram schematically showing another embodiment of the extension tube connected to the syringe.
Figure 9B:
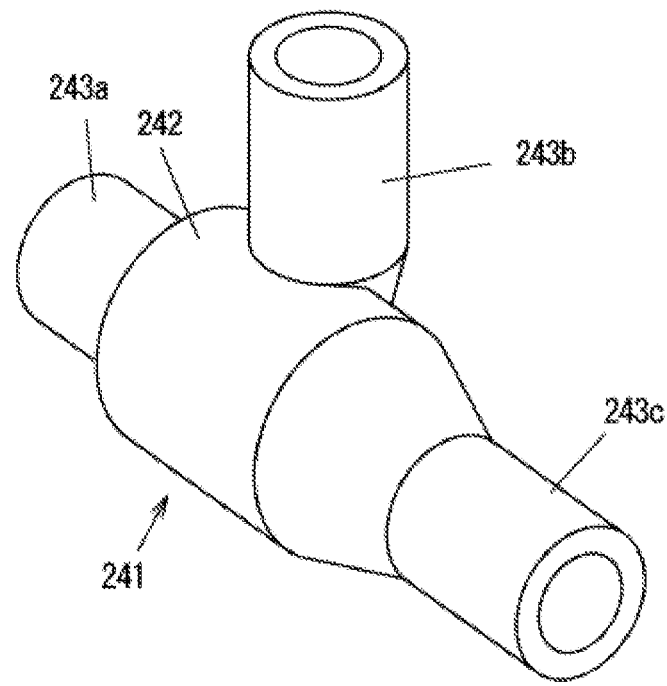
FIG. 9B is a perspective view of a mixing device provided in the extension tube shown in FIG. 9A.

The mixing device 241 will be described in detail below. As shown in FIGS. 9A and 9B, the mixing device 241 comprises a main body 242 including a first chamber that is a swirl flow generating chamber 242a which generates a swirl flow and a second chamber that is a constriction chamber 242b which concentrates the swirl flow in the axial direction. In this embodiment, the swirl flow generating chamber 242a has a cylindrical inner space, and the constriction chamber 242b has a conical inner space coaxial with the swirl flow generating chamber 242a. The cross-sectional shape in the lateral direction of the swirl flow generating chamber can be various shapes formed from a circle, an ellipse, and other curves. In addition, the swirl flow generating chamber can be configured to have a narrowed shape that narrows as it approaches the constriction chamber.

A conduit portion 243a to which the first tube 231a is connected is provided on the upstream side of the main body 242 of the mixing device 241, and a conduit portion 243c to which the third tube 231c is connected is provided on the downstream side. The conduit portion 243b to which the second tube 231b is connected is disposed at a position upstream from the center of the swirl flow generating chamber 242a (details below).

In this embodiment, the contrast medium flows from the conduit portion 243a and the physiological saline flows from the conduit portion 243b, and both chemical liquids are mixed in the mixing device. Thereafter, the mixed chemical liquid of the contrast medium and the physiological saline flows out from the conduit portion 243c as a liquid outlet.

The conduit portion 243a into which the chemical liquid having a large specific gravity flows is provided in the central portion of the wall surface on the upstream of the swirl flow generating chamber 242a on the upstream in the flow direction. The conduit portion 243c serving as the liquid outlet is provided so that the centerline of the conduit portion 243c and the centerline of the conduit portion 243a are aligned, that is, both are coaxial. By arranging them so as to have a coaxial axis, it is possible to increase the isotropic property of the vortex generated in the mixing device. That is, vortices can be generated uniformly in the space without stagnation, and the mixing efficiency can be improved.

Figure 9C:
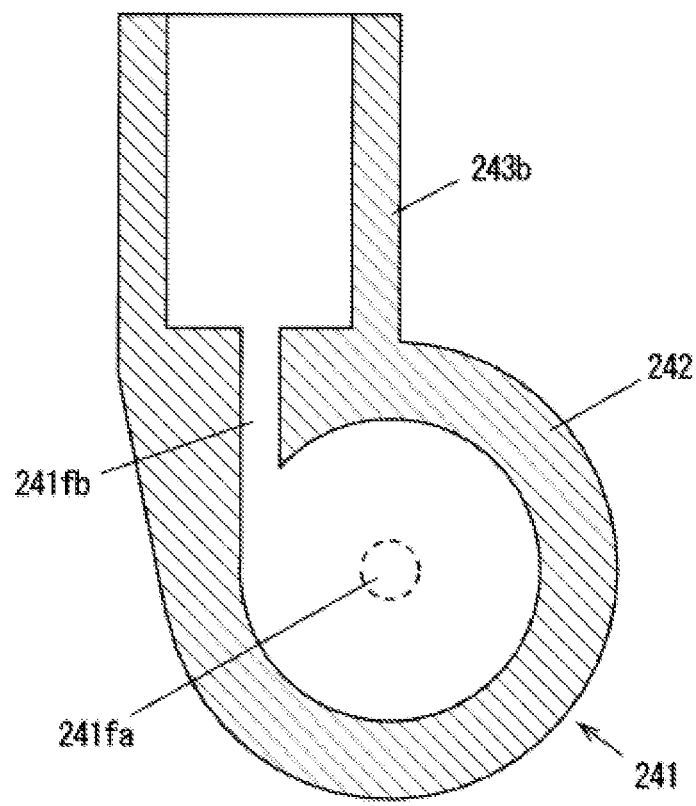
FIG. 9C is a cross-sectional view of a mixing device provided in the extension tube shown in FIG. 9A.

On the other hand, the conduit portion 243b into which the chemical liquid having a small specific gravity flows is disposed on the side surface of the swirl flow generating chamber 242a and extends in the tangential direction of the circumference of the swirl flow generating chamber 242a having a circular cross section. In other words, the conduit portion 243b is provided at a position shifted to the peripheral side from the central axis of the cylindrical space included in the swirl flow generating chamber 242a, and thereby, the swirl flow of the chemical liquid with small specific gravity which flowed in from the conduit portion 243b is generated. More specifically, as shown in FIG. 9C, the flow path 241fb is configured to extend in the circumferential tangential direction of the curved inner surface of the swirl flow generating chamber 242a, and thereby, the chemical liquid which flowed in from the flow path turns into a swirl flow. In addition, as is clear from the drawing, the constriction chamber 242b has an inclined inner surface that tapers downstream in the flow direction, so that the generated swirling flow is concentrated in the direction of the central axis of the vortex.

In addition, the conduit portion 243a into which the contrast medium flows is in communication with the swirl flow generating chamber 242a through the flow path 241fa. Thereby, the chemical liquid having a large specific gravity can be introduced into the swirling flow generating chamber in a direction parallel to the central axis of the swirling flow of the chemical liquid having a small specific gravity. That is, the chemical liquid having a large specific gravity is introduced in a direction parallel to the central axis of the cylindrical space included in the swirl flow generating chamber. The conduit portion into which the physiological saline flows is in communication with the swirl flow generation chamber through the flow path 241fb. For example, the inner diameter of the flow path 241fb may be smaller than the inner diameter of the flow path 241fa into which the contrast medium flows. According to such a configuration, when a chemical liquid is injected at a predetermined pressure, the flow rate of the chemical liquid having a small specific gravity flowing from the flow path 241fb having a relatively small cross-sectional area becomes higher than the flow rate of the chemical liquid having a large specific gravity. Therefore, it is possible to avoid a decrease in the mixing efficiency between the chemical liquids due to the attenuation of the inertial force of the swirling flow and the accompanying lack of swirling strength, which can occur when the flow rate of the chemical liquid having a small specific gravity is low.

In the mixing device 241 configured as described above, for example, when the contrast medium and the physiological saline are flowed into the device, the contrast medium that has flowed into the swirl flow generating chamber from the flow path 241fa flows toward the downstream in the axial direction. On the other hand, the physiological saline flowing into the swirl flow generation chamber from the flow path 241fb forms a swirl flow along the curved inner surface of the same chamber, and the swirl flow of the physiological saline is guided to the constriction chamber and concentrated in the central axis direction of the swirling flow. Such a vortex is known as a Rankine vortex, and the inertial force of the swirling flow can be concentrated in the vicinity of the rotation axis of the vortex.

When two chemical liquids are simultaneously injected using an extension tube having such a mixing device 241, both chemical liquids are well mixed. That is, in this example, it is possible to obtain a diluted contrast liquid in which the contrast medium and physiological saline are well mixed. As a result, since there is no unevenness in the concentration of the contrast medium, an excellent contrast effect can be expected as compared with a general extension tube having a T-shaped connector.

(Cooperation with Medical Network)

At least the chemical liquid injector 100 and the diagnostic imaging apparatus 500 may be connected to a medical network. Thereby, a diagnostic imaging apparatus, RIS (Radiology Information System), PACS (Picture Archiving and Communication System), HIS (Hospital Information System) and the like can store a flow rate, an injection time, an injection volume (if multiple injections were performed in a single examination and/or treatment, the injection volume per injection and the total volume of a series of injections) and an injection graph of the chemical liquid injected by the chemical liquid injector 100; a type of injected chemical liquid; an injection results including the mixing rate when performing the two-stage injection mode; and an imaging conditions in the fluoroscopic imaging device 500, as data via the network. As a result, the stored injection data is used for management of injection history. In particular, the injection volume or the like can be recorded in the chart information as a used chemical liquid and used for accounting. In addition, physical information such as the body weight, ID, name, examined region and examination method of the patient can be obtained from RIS, PACS, HIS, etc. to display on the chemical liquid injector, thereby an appropriate injection can be performed. Such information may be transmitted from the chemical liquid injector 100 to the RIS, PACKS, HIS, or the like via the diagnostic imaging apparatus 500, or may be transmitted directly from the chemical liquid injector 100 to the RIS, PACKS, HIS, or the like. When the chemical liquid injector 100 includes the RFID module 166, data transmitted to the RIS, PACKS, HIS, or the like can include data obtained from the RFID tag 352 by the RFID module 166.

Explanation of Symbols

100 Chemical liquid injector
101 Injection control unit

110 Injection head
112 Console
114 Main unit
120 Syringe receiver
123 Purge button
130a, 130b Piston driving mechanism
131 Presser
140 Clumper
164 RFID control circuit
165 Antenna
166 RFID module
200 Syringe assembly
220 Syringe
270 Protective cover
300 Extension tube
301 First tube
302 Second tube
303 Third tube
304 T-shaped connector
350 Container
352 RFID tag
400 Injection condition setting screen
500 Diagnostic imaging apparatus
510 Imaging control unit
520 Imaging operation unit

The invention claimed is:

1. A chemical liquid injector for injecting a chemical liquid filled in a container comprising:
   a first driving mechanism configured to make a first chemical liquid flow out of a first container filled with the first chemical liquid,
   a second driving mechanism configured to make a second chemical liquid flow out of a second container filled with the second chemical liquid,
   at least one data input interface which receives an input of data, and
   an injection controller configured to control an operation of at least the first driving mechanism and the second driving mechanism,
   wherein at least a multistage injection mode for performing a series of injection operation in a plurality of injection phases including a first phase and a second phase is set in the injection controller as one of at least one injection mode of the chemical liquid, and
   the injection controller is configured to:
   receive the input of a mixing rate of the first chemical liquid and the second chemical liquid through the data input interface for each of the plurality of injection phases in the multistage injection mode,
   set injection conditions of the first chemical liquid and the second chemical liquid so that the first chemical liquid and the second chemical liquid are injected at a mixing rate received by the injection controller, and
   control the operation of the first driving mechanism and the second driving mechanism according to injection conditions set by the injection controller, and
   wherein the mixing rate received by the injection controller is in a range of 0% to 100%, and
   the injection controller can set injection patterns including:
   (a) an injection pattern when the mixing rate of the first chemical liquid and the second chemical liquid is set to other than 0% in both the first phase and the second phase,
   (b) an injection pattern when the mixing rate of the second chemical liquid is set to 0% in the first phase, and the mixing rate of the first chemical liquid and the second chemical liquid is set to other than 0% in the second phase, and
   (c) an injection pattern when the mixing rate of the first chemical liquid and the second chemical liquid is set to other than 0% in the first phase, and the mixing rate of the second chemical liquid is set to 0% in the second phase.

2. The chemical liquid injector according to claim 1, wherein the mixing rate is a value calculated by a volume of the first chemical liquid/(a volume of the first chemical liquid+a volume of the second chemical liquid).

3. The chemical liquid injector according to claim 1, wherein the first chemical liquid is a contrast medium and the second chemical liquid is a physiological saline.

4. The chemical liquid injector according to claim 1, further comprising a touch panel including a display unit and the data input interface, and
   wherein the injection controller displays an injection condition setting screen including at least one icon for receiving the input of the data on the touch panel.

5. The chemical liquid injector according to claim 4, wherein the icon includes an icon for inputting the mixing rate for each of the plurality of injection phases.

6. The chemical liquid injector according to claim 1, further comprising a single injection head on which the first driving mechanism and the second driving mechanism are mounted.

7. The chemical liquid injector according to claim 1, further comprising a first injection head on which the first driving mechanism is mounted and a second injection head on which the second driving mechanism is mounted.

8. A chemical liquid injection system comprising:
   the chemical liquid injector according to claim 1,
   a first container and a second container detachably mounted on the chemical liquid injector, and
   an injection circuit connected to the first container and the second container.

9. The chemical liquid injection system according to claim 8, wherein at least one of the first container and the second container is a container filled with a contrast medium.

10. The chemical liquid injection system according to claim 8, wherein the injection circuit includes an extracorporeal circuit portion branched so that a proximal side is connected to the first container and the second container.

11. A diagnostic imaging system comprising:
   the chemical liquid injection system according to claim 8,
   a diagnostic imaging apparatus for obtaining a medical image from a patient into which a chemical liquid has been injected by the chemical liquid injection system.

12. The diagnostic imaging system according to claim 11, wherein the diagnostic imaging apparatus is an angiographic apparatus.

13. An operation method of a chemical liquid injector for injecting a chemical liquid filled in a container comprising:
   a first driving mechanism configured to make a first chemical liquid flow out of a first container filled with the first chemical liquid,
   a second driving mechanism configured to make a second chemical liquid flow out of a second container filled with the second chemical liquid,
   at least one data input interface which receives an input of data, and
   an injection controller configured to control an operation of at least the first driving mechanism and the second driving mechanism, wherein at least a multistage injection mode for performing a series of injection operation in a plurality of injection phases including a first phase and a second phase is set in the injection controller as one of at least one injection mode of the chemical liquid, the operation method comprising:

receiving the input of a mixing rate of the first chemical liquid and the second chemical liquid through the data input interface for each of the plurality of injection phases in the multistage injection mode by the injection controller, setting injection conditions of the first chemical liquid and the second chemical liquid by the injection controller so that the first chemical liquid and the second chemical liquid are injected at the received mixing rate, controlling the operation of the first driving mechanism and the second driving mechanism by the injection controller according to the set injection conditions, and wherein receiving the input of the mixing rate includes receiving the mixing rate in a range of 0% to 100%, and in setting injection conditions, injection patterns including (a) an injection pattern when the mixing rate of the first chemical liquid and the second chemical liquid is set to other than 0% in both the first phase and the second phase, (b) an injection pattern when the mixing rate of the second chemical liquid is set to 0% in the first phase, and the mixing rate of the first chemical liquid and the second chemical liquid is set to other than 0% in the second phase, and (c) an injection pattern when the mixing rate of the first chemical liquid and the second chemical liquid is set to other than 0% in the first phase, and the mixing rate of the second chemical liquid is set to 0% in the second phase can be set.

14. The operation method of the chemical liquid injector according to claim 13, wherein receiving the input of a mixing rate includes calculating the mixing rate by a volume of the first chemical liquid/(a volume of the first chemical liquid+a volume of the second chemical liquid) by the injection controller.

15. The operation method according to claim 13, wherein the chemical liquid injector further comprises a touch panel including a display unit and the data input interface, and wherein receiving the input of the mixing rate includes displaying an injection condition setting screen including at least one icon for receiving the input of the data on the touch panel by the injection controller.

16. The operation method according to claim 15, wherein the icon includes an icon for inputting the mixing rate for each of the plurality of injection phases.

* * * * *